US008175816B2

(12) United States Patent
Barrett, Jr. et al.

(10) Patent No.: US 8,175,816 B2
(45) Date of Patent: May 8, 2012

(54) SYSTEM AND METHOD FOR ANALYZING METABOLOMIC DATA

(75) Inventors: Thomas Henry Barrett, Jr., Raleigh, NC (US); Corey Donald DeHaven, Raleigh, NC (US); Danny C. Alexander, Cary, NC (US); Sarada Tanikella, Morrisville, NC (US)

(73) Assignee: Metabolon Inc., Durham, NC (US)

( * ) Notice: Subject to any disclaimer, the term of this patent is extended or adjusted under 35 U.S.C. 154(b) by 0 days.

(21) Appl. No.: 13/084,999

(22) Filed: Apr. 12, 2011

(65) Prior Publication Data

US 2011/0307180 A1  Dec. 15, 2011

Related U.S. Application Data

(60) Division of application No. 12/245,862, filed on Oct. 6, 2008, now Pat. No. 7,949,475, which is a continuation-in-part of application No. 11/462,838, filed on Aug. 7, 2006, now Pat. No. 7,433,787.

(60) Provisional application No. 60/706,459, filed on Aug. 8, 2005.

(51) Int. Cl.
*G01N 31/00* (2006.01)
(52) U.S. Cl. ............................................. 702/22; 703/1
(58) Field of Classification Search .................... 702/22, 702/182–185; 703/1
See application file for complete search history.

(56) References Cited

U.S. PATENT DOCUMENTS

| | | |
|---|---|---|
| 6,181,134 B1 | 1/2001 | Wald |
| 6,898,533 B1 | 5/2005 | Miller et al. |
| 7,005,255 B2 | 2/2006 | Kaddurah-Daouk et al. |
| 7,329,489 B2 | 2/2008 | Kaddurah-Daouk et al. |

(Continued)

FOREIGN PATENT DOCUMENTS

WO  WO 2004/106915 A1  12/2004

OTHER PUBLICATIONS

Deshpande et al.; "Automated and Rapid Bacterial Identification Using LC-Mass Spectrometry With a Relational Database Management System" *Computational Systems Bioinformatics Conference*, 2004. CSB 2004, USA.

(Continued)

*Primary Examiner* — Edward Raymond
(74) *Attorney, Agent, or Firm* — Womble Carlyle Sandridge & Rice, LLP

(57) ABSTRACT

The present invention generates a visual display of metabolomic data compiled by a database and associated processor. More particularly, the present invention provides a database for automatically receiving a three-dimensional spectrometry data set for a group of samples. The present invention also provides a processor device for manipulating the data sets to produce plots that are directly comparable to a plurality of characteristic plots corresponding to a plurality of selected metabolites. Furthermore, the processor device may generate a visual display indicating the presence of the selected metabolites across the group of samples. Thus, the present invention enables a user to analyze a series of complex data sets in a visual display that may indicate the presence of the selected metabolites across the group of samples. Furthermore, the visual display generated by embodiments of the present invention also expedites the subjective analysis of the spectrometry data sets.

15 Claims, 14 Drawing Sheets

U.S. PATENT DOCUMENTS

| | | |
|---|---|---|
| 2001/0016314 A1 | 8/2001 | Anderson et al. |
| 2001/0056485 A1 | 12/2001 | Barrett, Jr. et al. |
| 2003/0139885 A1 | 7/2003 | Brock et al. |
| 2004/0143461 A1* | 7/2004 | Watkins ............................ 705/2 |
| 2005/0116159 A1 | 6/2005 | Becker et al. |
| 2005/0209789 A1 | 9/2005 | Hastings |
| 2005/0288872 A1 | 12/2005 | Old et al. |
| 2006/0151688 A1* | 7/2006 | Castro-Perez et al. ........ 250/284 |
| 2006/0172429 A1 | 8/2006 | Nilsson et al. |
| 2006/0188868 A1 | 8/2006 | Lloyd et al. |

OTHER PUBLICATIONS

Gamache et al.; "Metabolomic Applications of Electrochemistry/Mass Spectrometry" *J. Am Soc Mass Spectrom*, 2004, pp. 1717-1726, vol. 15, No. 12, USA.

Wagner et al.; "Construction and Application of a Mass Spectral and Retention Time Index Database Generated From Plant GC/EI-TOF-MS Metabolite Profiles"; *Phytochemistry*, 2003, pp. 887-900, vol. 62, No. 6.

* cited by examiner

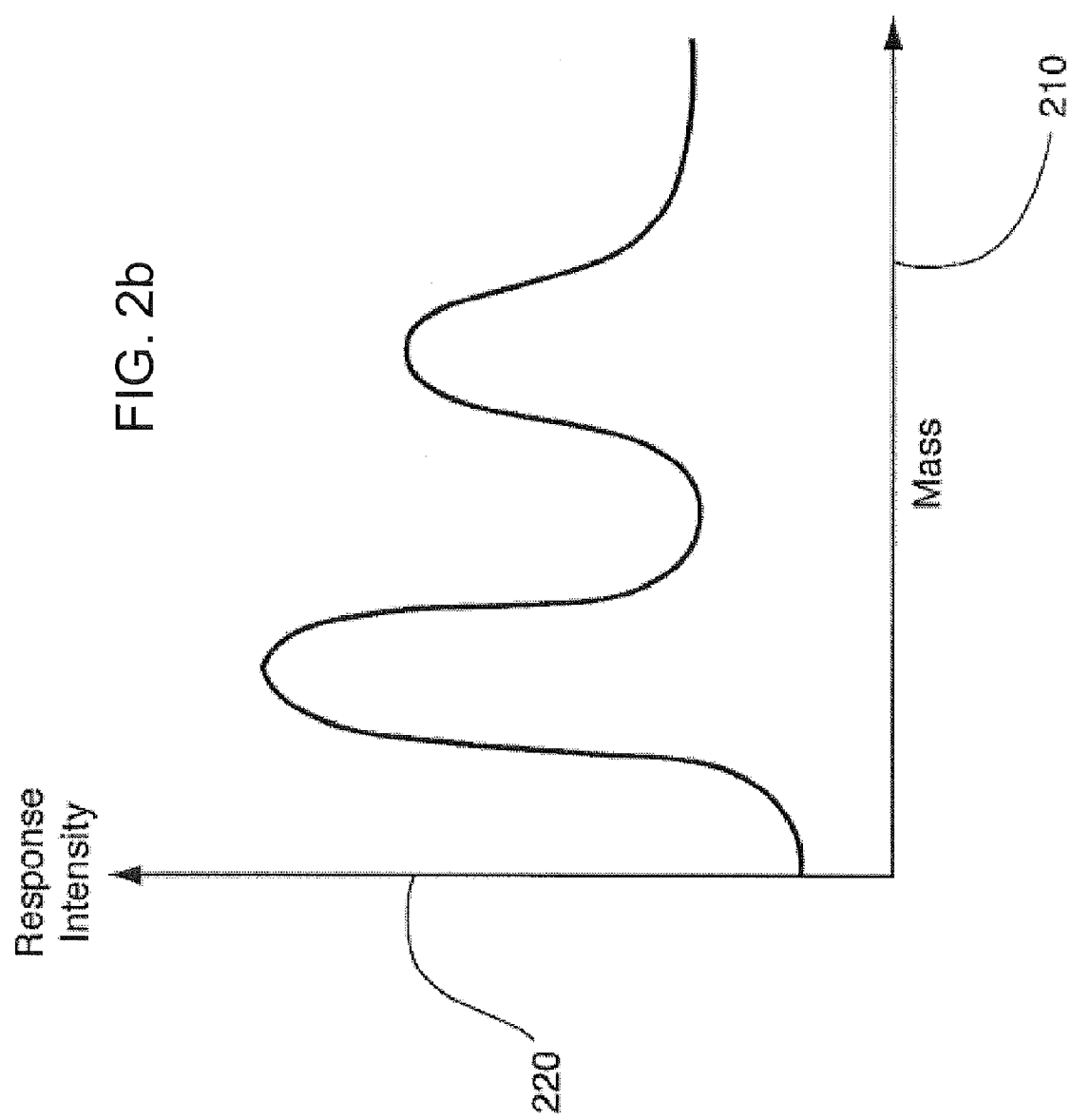

FIG. 8

SYSTEM AND METHOD FOR ANALYZING METABOLOMIC DATA

CROSS-REFERENCE TO RELATED APPLICATION

This application is a divisional of U.S. application Ser. No. 12/245,862, now U.S. Pat. No. 7,949,475 filed Oct. 6, 2008, which is a continuation-in-part of U.S. patent application Ser. No. 11/462,838, now U.S. Pat. No. 7,433,787 filed Aug. 7, 2006, which claims the benefit of U.S. Provisional Application No. 60/706,459, filed Aug. 8, 2005, all of which are incorporated by reference herein in their entirety.

BACKGROUND OF THE INVENTION

1. Field of the Invention

The present invention relates to the field of metabolomics, which is the study of small molecules produced by an organism's metabolic processes. More particularly, the embodiments of the present invention are adapted to compile and compare metabolomic data received from a spectrometry device across a plurality of samples. Furthermore, embodiments of the present invention may also provide for the display of a visual indication of the presence of selected metabolites in each of the plurality of samples such that metabolomic data may be subjectively analyzed by a user across the plurality of samples.

2. Description of Related Art

Metabolomics is the study of the small molecules, or metabolites, contained in a cell, tissue or organ (including fluids) and involved in primary and intermediary metabolism. The term "metabolome" refers to the collection of metabolites present in an organism. The human metabolome encompasses native small molecules (natively biosynthesizeable, non-polymeric compounds) that are participants in general metabolic reactions and that are required for the maintenance, growth and normal function of a cell. Thus, metabolomics is a direct observation of the status of cellular physiology, and may thus be predictive of disease in a given organism. Subtle biochemical changes (including the presence of selected metabolites) are inherent in a given disease. Therefore, the accurate mapping of these changes to known pathways may allow researchers to build a biochemical hypothesis for a disease. Based on this hypothesis, the enzymes and proteins critical to the disease can be uncovered such that disease targets may be identified for treatment with targeted pharmaceutical compounds or other therapy.

Molecular biology techniques for uncovering the biochemical processes underlying disease have been centered on the genome, which consists of the genes that make up DNA, which is transcribed into RNA and then translated to proteins, which then make up the small molecules of the human metabolome. While genomics (study of the DNA-level biochemistry), transcript profiling (study of the RNA-level biochemistry), and proteomics (study of the protein-level biochemistry) are useful for identification of disease pathways, these methods are complicated by the fact that there exist over 25,000 genes, 100,000 to 200,000 RNA transcripts and up to 1,000,000 proteins in human cells. However, it is estimated that there may be as few as 2,500 small molecules in the human metabolome.

Thus, metabolomic technology provides a significant leap beyond genomics, transcript profiling, and/or proteomics. With metabolomics, metabolites, and their role in the metabolism may be readily identified. In this context, the identification of disease targets may be expedited with greater accuracy relative to other known methods. The collection of metabolomic data for use in identifying disease pathways is generally known in the art, as described generally, for example, in U.S. Pat. Nos. 7,005,255 and 7,329,489 to Metabolon, Inc., each entitled Methods for Drug Discovery, Disease Treatment, and Diagnosis Using Metabolomics. Additional uses for metabolomics data are described therein and include, for example, determining response to a therapeutic agent (i.e., drug) or other xenobiotics, monitoring drug response, determining drug safety, and drug discovery. However, the collection and sorting of metabolomic data taken from a variety of samples (e.g., from a patient population) consumes large amounts of time and computational power. For example, according to some known metabolomic techniques, spectrometry data for certain samples is collected and plotted in three dimensions and stored in an individual file corresponding to each sample. This data is then individually compared to data corresponding to a plurality of known metabolites in order to identify known metabolites that may be disease targets. The data may also be used for identification of toxic agents and/or drug metabolites. Furthermore such data may also be used to monitor the effects of xenobiotics. However, conventional "file-based" methods (referring to the data file generated for each sample) require the use of large amounts of computing power and memory assets to handle the screening of large numbers of known metabolites. Furthermore, "file-based" data handling does not lend itself to the compilation of sample population data across a number of samples because, according to known metabolomic data handling techniques, each sample is analyzed independently, without taking into account subtle changes in metabolite composition that may be more readily detectable across a sample population. Furthermore, existing "file-based" method have other limitations including: limited security and audit ability; poor data set consistency across multiple file copies; and individual files do not support multiple indices (example day collected, sample ID, control vs. treated, drug dose, etc) such that all files must be scanned when only a subset is desired.

These limitations in current metabolomic data analysis techniques may lead to the discarding of potentially relevant and/or valuable metabolomic data that may be used to identify and classify particular metabolites as disease targets. Specifically, spectrometry data corresponding to a number of samples (such as tissue samples from individual human subjects) generally results in a large data file corresponding to each sample, wherein each data file must then be subjected to a screening process using a library of known metabolites. However, conventional systems do not readily allow for the consolidation of spectrometry data from a number of samples for the subjective evaluation of the data generated by the spectrometry processes. Thus, while a single file corresponding to an individual sample may be inconclusive, such data may be more telling if viewed subjectively in a succinct format with respect to other samples within a sample population.

Therefore, there exists a need for an improved system to solve the technical problems outlined above that are associated with conventional metabolomic data analysis systems. More particularly, there exists a need for a system capable of automatically receiving spectrometry data without the need to generate a separate data file for each sample. There also exists a need for a system capable of converting three-dimensional data sets into a corresponding two-dimensional data set and associated plot, which may then be compared to a plurality of characteristic plots corresponding to selected metabolites. In addition, there exists a need for a system for allowing a user to subjectively evaluate the spectrometry data across a plurality of samples to identify selected metabolites, for allowing the user to verify or otherwise determine the confidence in the identification of the selected metabolites, for allowing the user to examine the data associated with the identification of the selected metabolites, and for allowing the user to determine additional information related to the identified selected metabolites.

BRIEF SUMMARY OF THE INVENTION

The needs outlined above are met by the present invention which, in various embodiments, provides systems and associated methods that overcome many of the technical problems discussed above, as well other technical problems, with regard to the automated analysis (i.e., compilation, translation, and concise display) of metabolomic data by conventional spectrometry data analysis systems.

More particularly, one embodiment provides a method of analyzing metabolomics data, and a computer program product embodying such a method, wherein a three-dimensional data set of metabolomics data corresponding to each of a plurality of samples, is automatically received in a database from each of a first data source and a second data source. For the metabolomics data from each of the first and second data sources, the three-dimensional data set is converted into at least one corresponding two-dimensional data set for each of the plurality of samples, and the at least one two-dimensional data set for each of the plurality of samples is plotted. The at least one plotted two-dimensional data set for each of the plurality of samples is compared to a plurality of characteristic plots corresponding to a plurality of selected metabolites so as to screen the plurality of samples by associating at least one of the plurality of selected metabolites with the at least one plotted two-dimensional data set for each of the plurality of samples. For the screened plurality of samples determined to have the at least one of the plurality of selected metabolites associated therewith, the at least one plotted two-dimensional data set for each of the screened plurality of samples is compared, across the screened plurality of samples, so as to determine a trend of the associated at least one of the plurality of selected metabolites, across the screened plurality of samples. A visual indication of the comparison of the at least one plotted two-dimensional data set for each of the screened plurality of samples, across a plurality of the screened plurality of samples, is then displayed to visually indicate the screened plurality of samples determined to have the at least one of the plurality of selected metabolites associated therewith, and the trend corresponding thereto, across the plurality of the screened plurality of samples, for the metabolomics data from each of the first and second data sources. The first and second data sources are then compared with respect to the at least one of the plurality of selected metabolites determined to be included in the metabolomics data and the trend across the screened plurality of samples associated therewith so as to determine an identity confidence measure associated with the at least one of the plurality of selected metabolites.

Another aspect of the present invention provides a system for analyzing metabolomics data, comprising a database in communication with each of a first data source and a second data source, wherein the database is configured to automatically receive a three-dimensional data set of metabolomics data corresponding to each of a plurality of samples, from each of the first and second data sources. A processor device is in communication with said database, wherein said processor device is configured, for the metabolomics data from each of the first and second data sources, to convert the three-dimensional data set into at least one corresponding two-dimensional data set for each of the plurality of samples; plot the at least one two-dimensional data set for each of the plurality of samples; compare the at least one plotted two-dimensional data set for each of the plurality of samples to a plurality of characteristic plots corresponding to a plurality of selected metabolites so as to screen the plurality of samples by associating at least one of the plurality of selected metabolites with the at least one plotted two-dimensional data set for each of the plurality of samples; and compare, for the screened plurality of samples determined to have the at least one of the plurality of selected metabolites associated therewith, the at least one plotted two-dimensional data set for each of the screened plurality of samples, across the screened plurality of samples, so as to determine a trend of the associated at least one of the plurality of selected metabolites, across the screened plurality of samples. A user interface is in communication with said database and said processor device, wherein the user interface is configured to display a visual indication of the comparison of the at least one plotted two-dimensional data set for each of the screened plurality of samples, across a plurality of the screened plurality of samples, to visually indicate the screened plurality of samples determined to have the at least one of the plurality of selected metabolites associated therewith, and the trend corresponding thereto, across the plurality of the screened plurality of samples, for the metabolomics data from each of the first and second data sources. The displayed visual indication is further configured to facilitate determination of an identity confidence measure associated with the at least one of the plurality of selected metabolites from a comparison of the first and second data sources with respect to the at least one of the plurality of selected metabolites determined to be included in the metabolomics data and the trend across the screened plurality of samples associated therewith.

Yet another aspect of the present invention provides a method for analyzing metabolomics data, and a computer program product embodying such a method, wherein a three-dimensional data set corresponding to each of a plurality of samples is automatically received in a database, wherein each of the three-dimensional data sets has at least one of an experimental factor, a sample factor, and a process factor associated therewith. The three-dimensional data set is converted into at least one corresponding two-dimensional data set for each of the plurality of samples, such that the respective at, least one of an experimental factor, a sample factor, and a process factor remains associated with the corresponding two-dimensional data set. The at least one two-dimensional data set is plotted for each of the plurality of samples. The at least one plotted two-dimensional data set for each of the plurality of samples is compared to a plurality of characteristic plots corresponding to a plurality of selected metabolites so as to screen the plurality of samples by associating at least one of the plurality of selected metabolites with the at least one plotted two-dimensional data set for each of the plurality of samples. For the screened plurality of samples determined to have the at least one of the plurality of selected metabolites associated therewith, the at least one plotted two-dimensional data set for each of the screened plurality of samples is compared, across the screened plurality of samples, so as to determine a trend of the associated at least one of the plurality of selected metabolites, across the screened plurality of samples. A visual indication of the comparison of the at least one plotted two-dimensional data set for each of the screened plurality of samples is compared, across a plurality of the screened plurality of samples, to visually indicate the screened plurality of samples determined to have the at least one of the plurality of selected metabolites associated therewith, and the trend corresponding thereto, across the plurality of the screened plurality of samples. The comparison of the at least one plotted two-dimensional data set for each of the screened plurality of samples is then sorted, across a plurality of the screened plurality of samples, by the at least one of an experimental factor, a sample factor, and a process factor associated with the corresponding two-dimensional data set, so as to visually indicate the screened plurality of samples determined to have the at least one of the plurality of selected metabolites associated therewith, and the trend corresponding thereto, across the plurality of the screened plurality of samples, in relation to the at least one of an experimental factor, a sample factor, and a process factor.

Still another aspect of the present invention provides a system for analyzing metabolomics data, comprising a database configured to automatically receive a three-dimensional data set of metabolomics data corresponding to each of a plurality of samples, wherein each of the three-dimensional data sets has at least one of an experimental factor, a sample factor, and a process factor associated therewith. A processor device is in communication with said database, and is configured to convert the three-dimensional data set into at least one corresponding two-dimensional data set for each of the plurality of samples, such that the respective at least one of an experimental factor, a sample factor, and a process factor remains associated with the corresponding two-dimensional data set; plot the at least one two-dimensional data set for each of the plurality of samples; compare the at least one plotted two-dimensional data set for each of the plurality of samples to a plurality of characteristic plots corresponding to a plurality of selected metabolites so as to screen the plurality of samples by associating at least one of the plurality of selected metabolites with the at least one plotted two-dimensional data set for each of the plurality of samples; and compare, for the screened plurality of samples determined to have the at least one of the plurality of selected metabolites associated therewith, the at least one plotted two-dimensional data set for each of the screened plurality of samples, across the screened plurality of samples, so as to determine a trend of the associated at least one of the plurality of selected metabolites, across the screened plurality of samples. A user interface is in communication with said database and said processor device, wherein the user interface is configured to display a visual indication of the comparison of the at least one plotted two-dimensional data set for each of the screened plurality of samples, across a plurality of the screened plurality of samples, to visually indicate the screened plurality of samples determined to have the at least one of the plurality of selected metabolites associated therewith, and the trend corresponding thereto, across the plurality of the screened plurality of samples. The processor device is further configured to cooperate with the user interface to sort the comparison of the at least one plotted two-dimensional data set for each of the screened plurality of samples, across a plurality of the screened plurality of samples, by the at least one of an experimental factor, a sample factor, and a process factor associated with the corresponding two-dimensional data set, so as to visually indicate the screened plurality of samples determined to have the at least one of the plurality of selected metabolites associated therewith, and the trend corresponding thereto, across the plurality of the screened plurality of samples, in relation to the at least one of an experimental factor, a sample factor, and a process factor.

Thus the systems, methods, and computer program products for analyzing metabolomics data across a plurality of samples, as disclosed in conjunction with the embodiments of the present invention, provide many advantages that may include, but are not limited to: automatically compiling and indexing complex three-dimensional spectrometry data sets for a plurality of samples so as to be capable of generating a sample population data set; converting the complex three dimensional data sets into two dimensional data sets and corresponding data plots that are more easily comparable to a library of data plots corresponding to a plurality of selected metabolites of interest; providing a graphical representation of the spectrometry data analyses used to identify metabolites of interest; and providing a graphical representation of the compiled data across a population of samples such that the user of the system of the present invention may subjectively evaluate the spectrometry data and evaluate only those samples exhibiting a variance that may be indicative of the absence and/or presence of a selected metabolite, without the need for opening a plurality of individual data files corresponding to each particular sample under examination. In doing so, embodiments of the present invention, for example, advantageously allow a user to subjectively evaluate the spectrometry data across a plurality of samples to identify selected metabolites, allow the user to verify or otherwise determine the confidence in the identification of the selected metabolites, allow the user to examine the data associated with the identification of the selected metabolites, and allow the user to determine additional information related to the identified selected metabolites.

These advantages and others that will be evident to those skilled in the art are provided in the system, method, and computer program product embodiments of the present invention. Importantly, all of these advantages allow the system to display metabolomic analysis results to a user in a compact format that spans a "fourth dimension" across the population of samples. Because, analytical results data spanning across the sample population is made more readily evident to the user in a graphical format, along with the identification of metabolites of interest as potential disease targets, the user is better able to determine the presence and/or absence of selected metabolites and/or chemical components within or otherwise associated with the samples. Furthermore, because additional sample population data is provided, the embodiments of the present invention are less likely to discount potentially valuable spectrometry results that may be discounted when viewed independently from the sample population.

BRIEF DESCRIPTION OF THE SEVERAL VIEWS OF THE DRAWINGS

Figure 1:
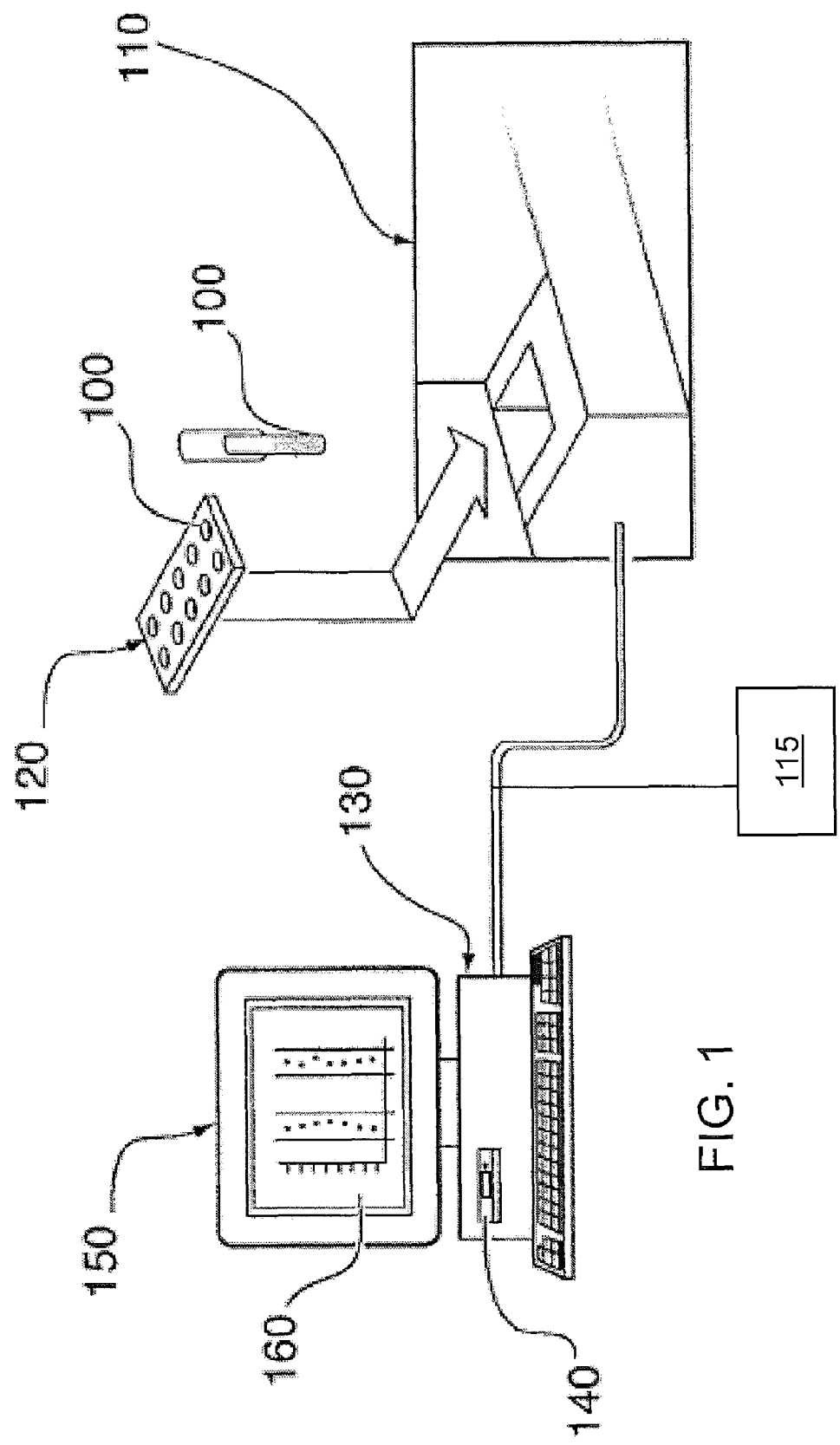
Figure 2A:
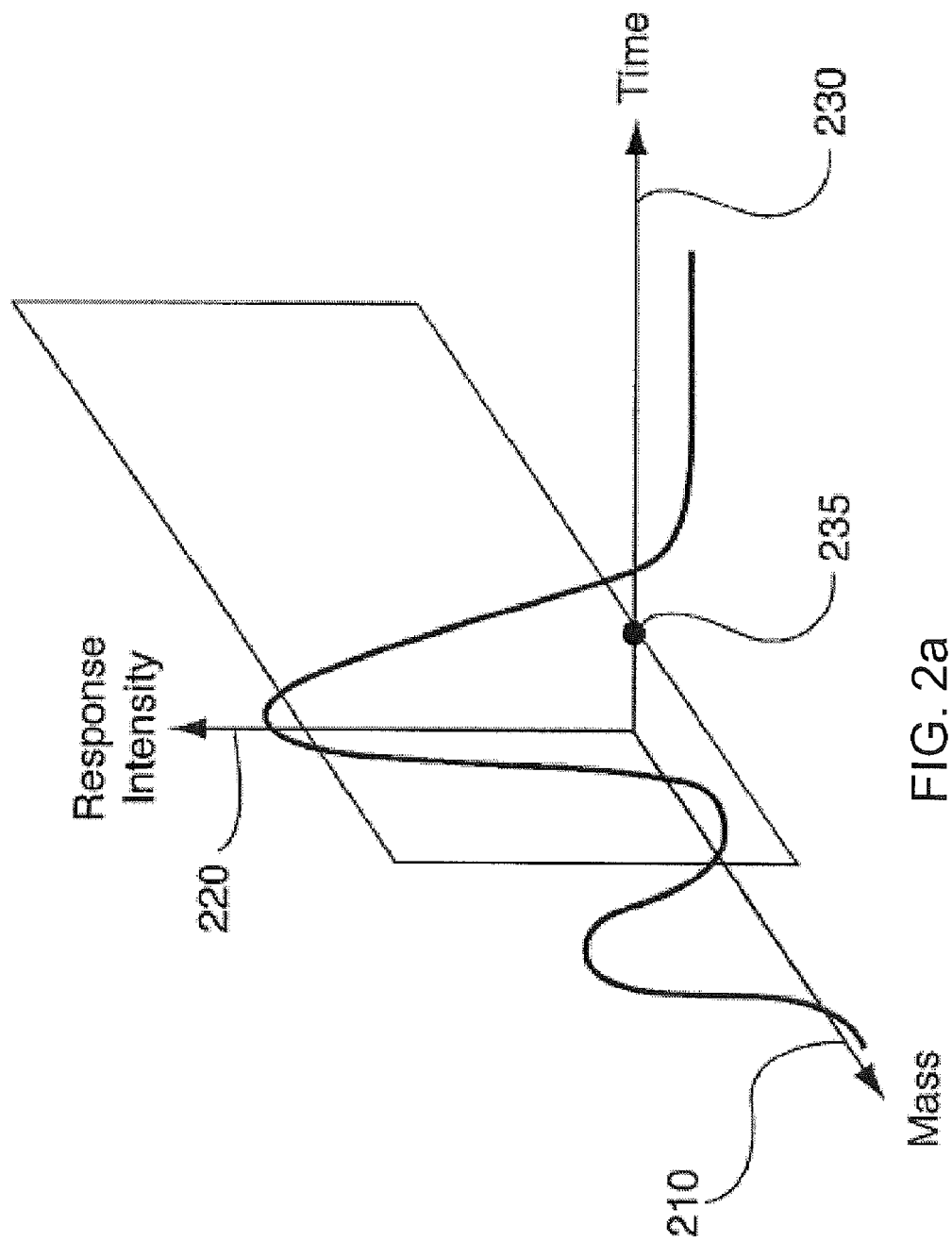
Figure 2C:
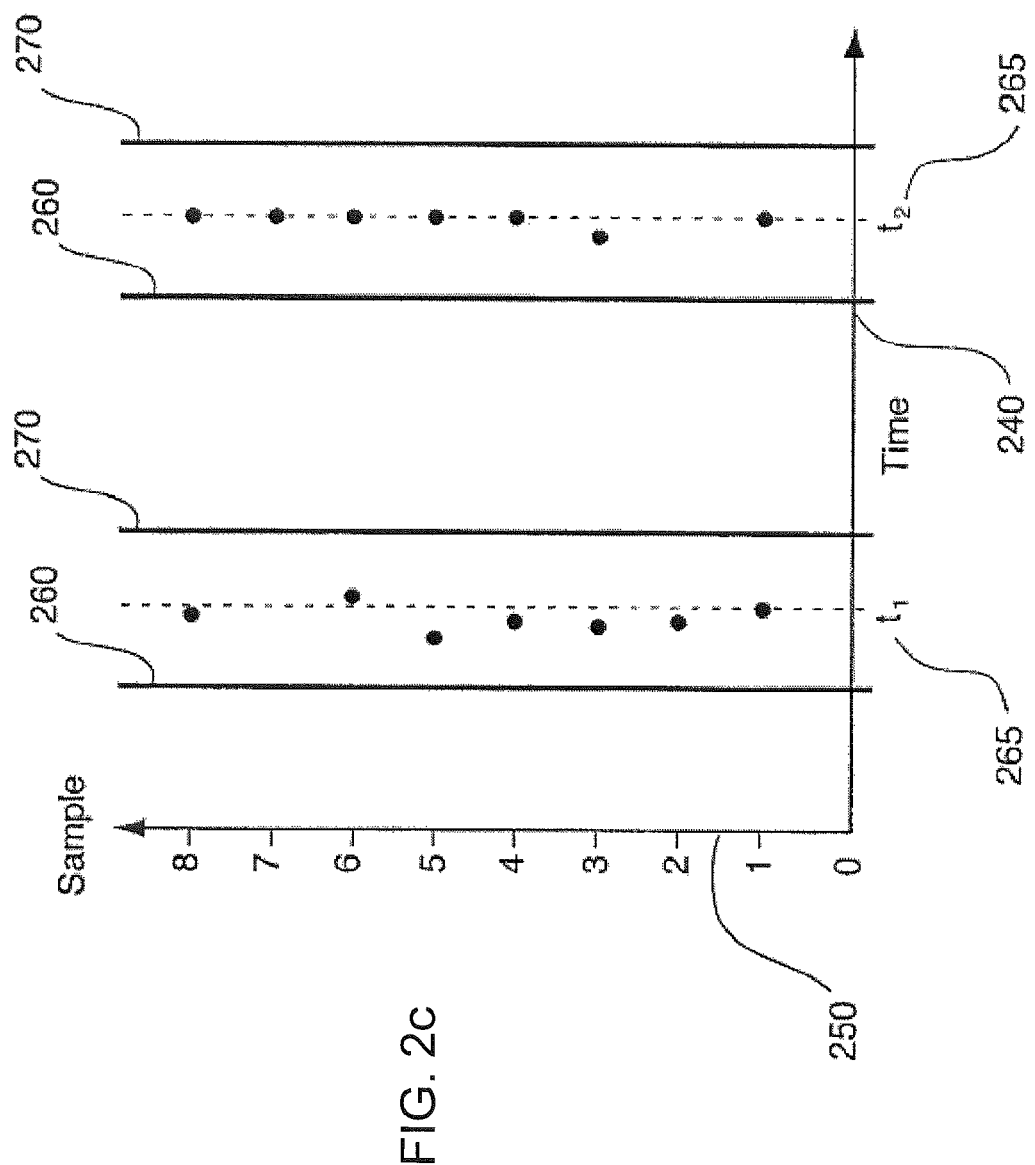
Figure 3:
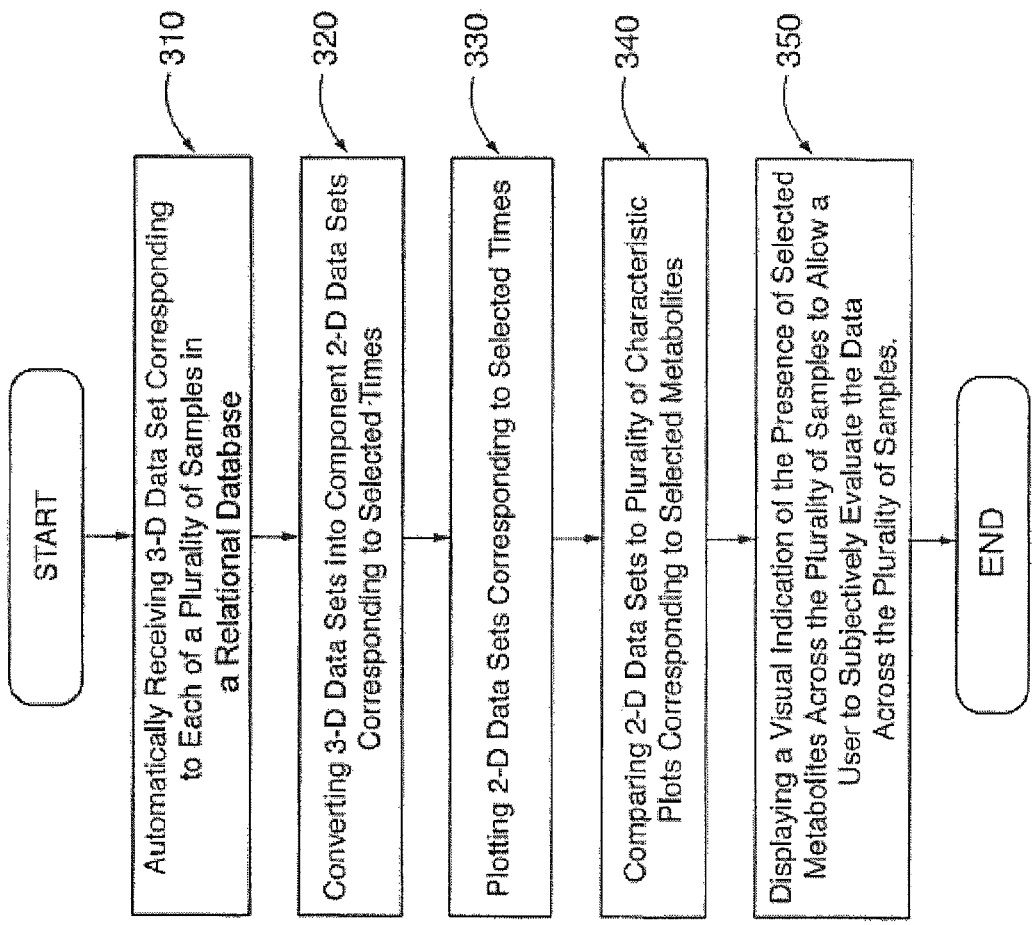
Figure 4:
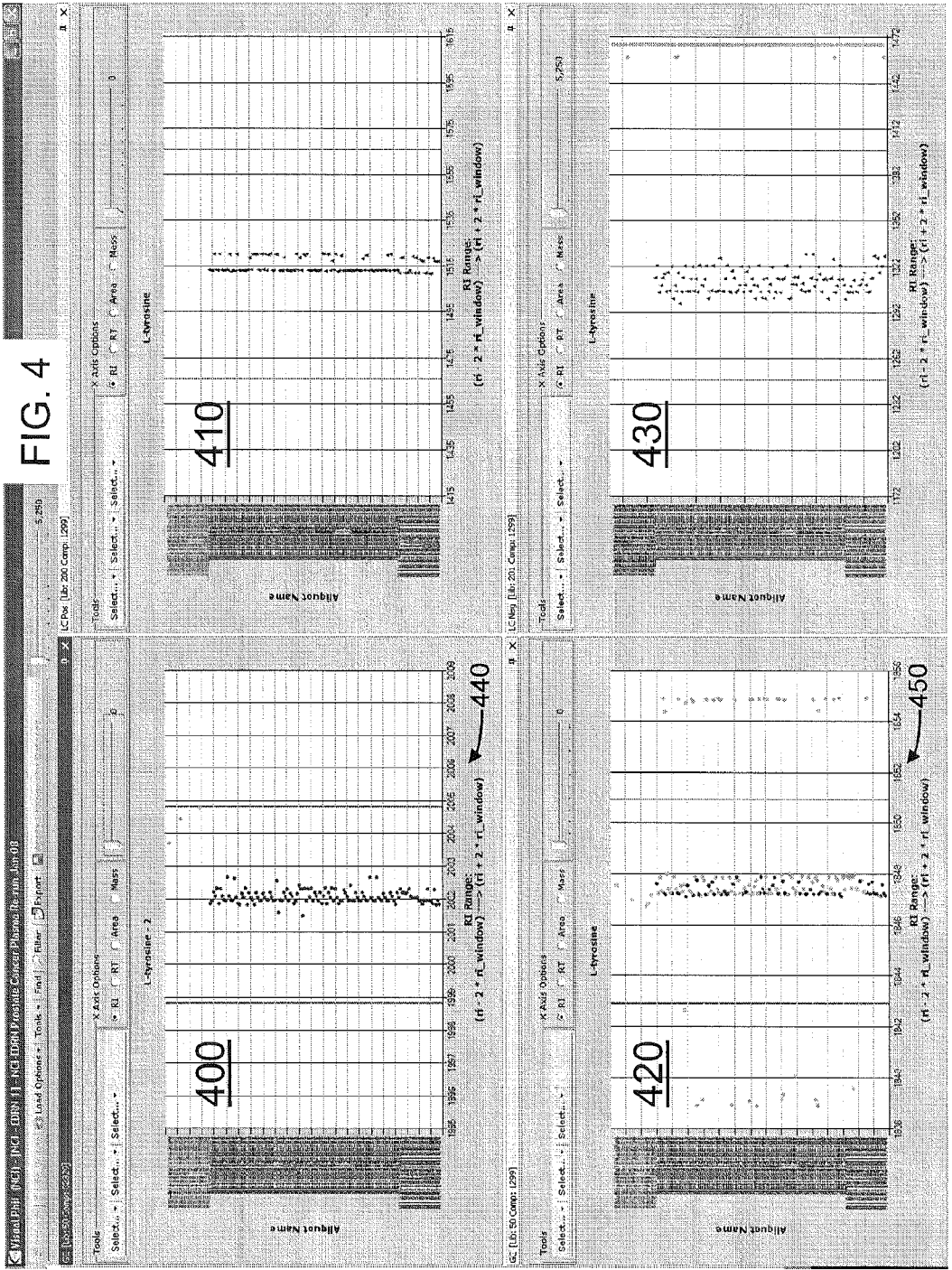
Figure 5:
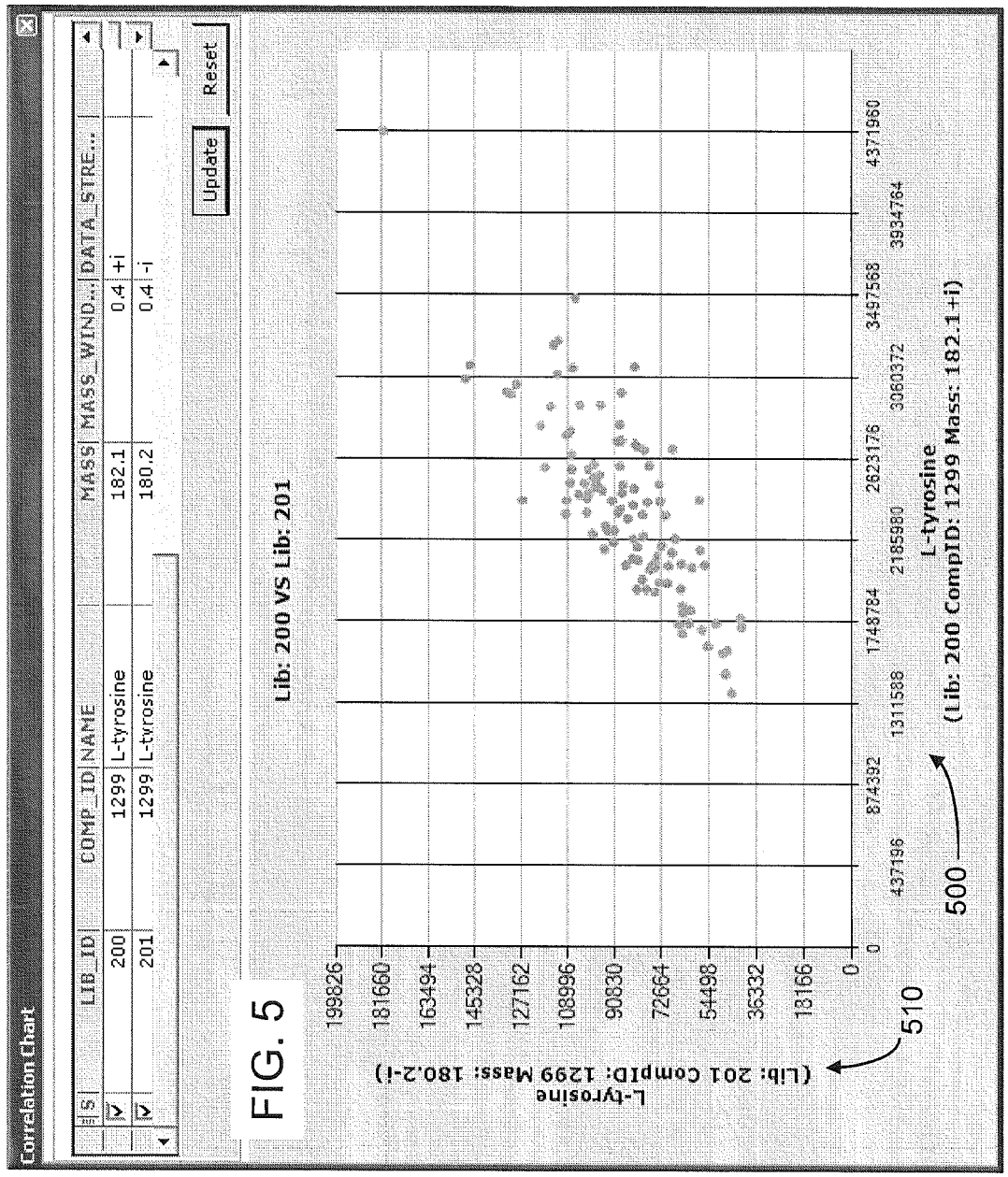
Figure 6:
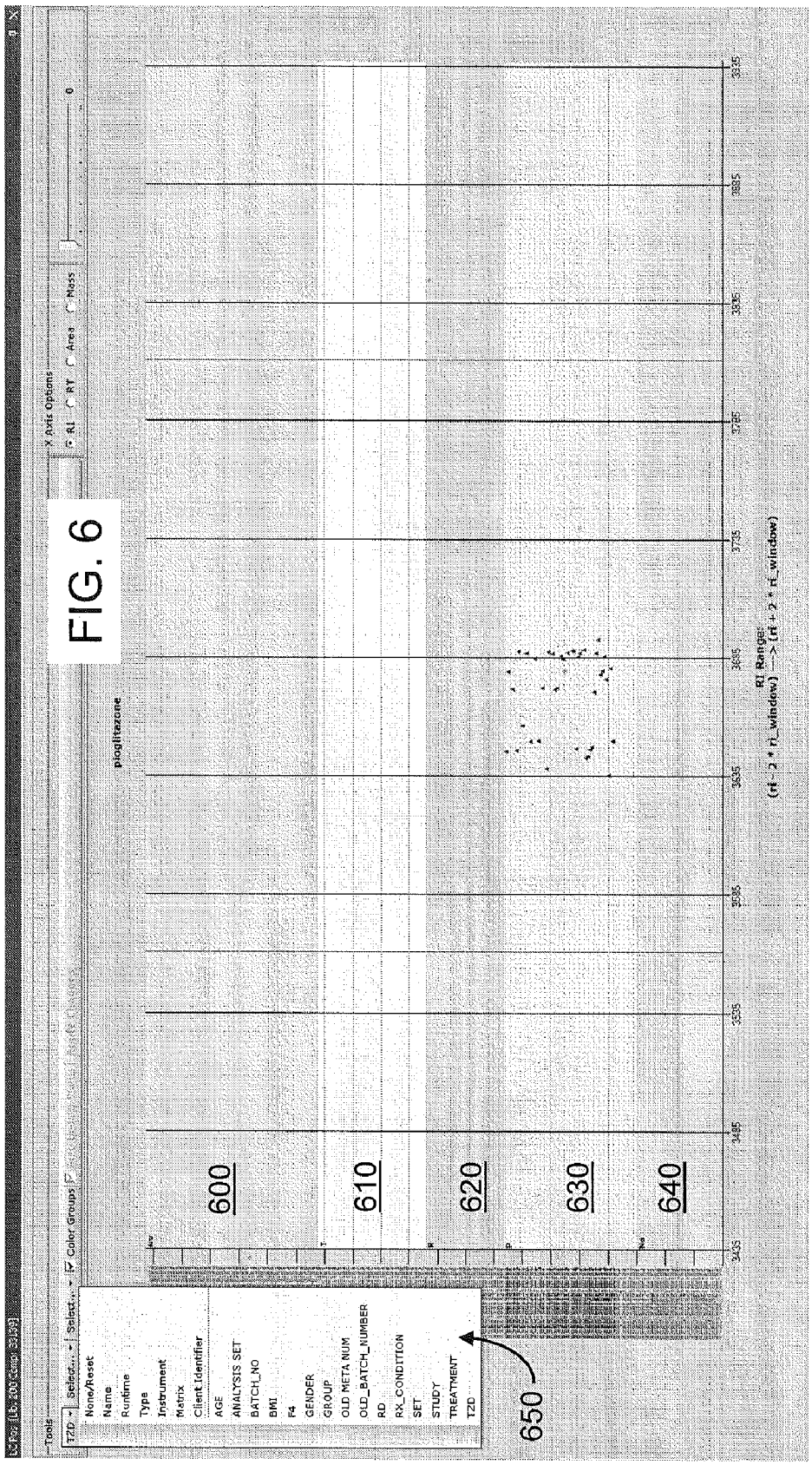
Figure 7A:
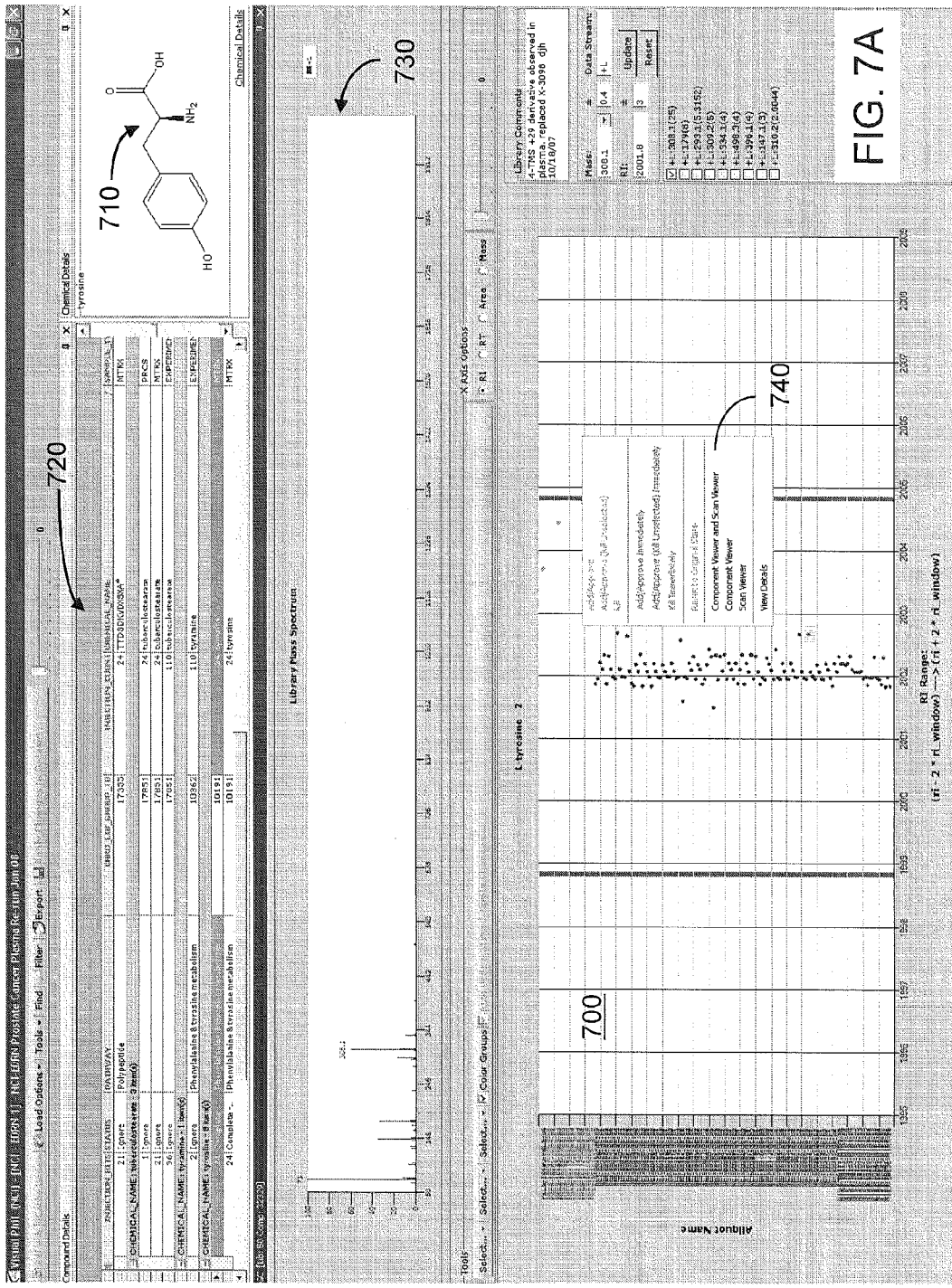
Figure 7B:
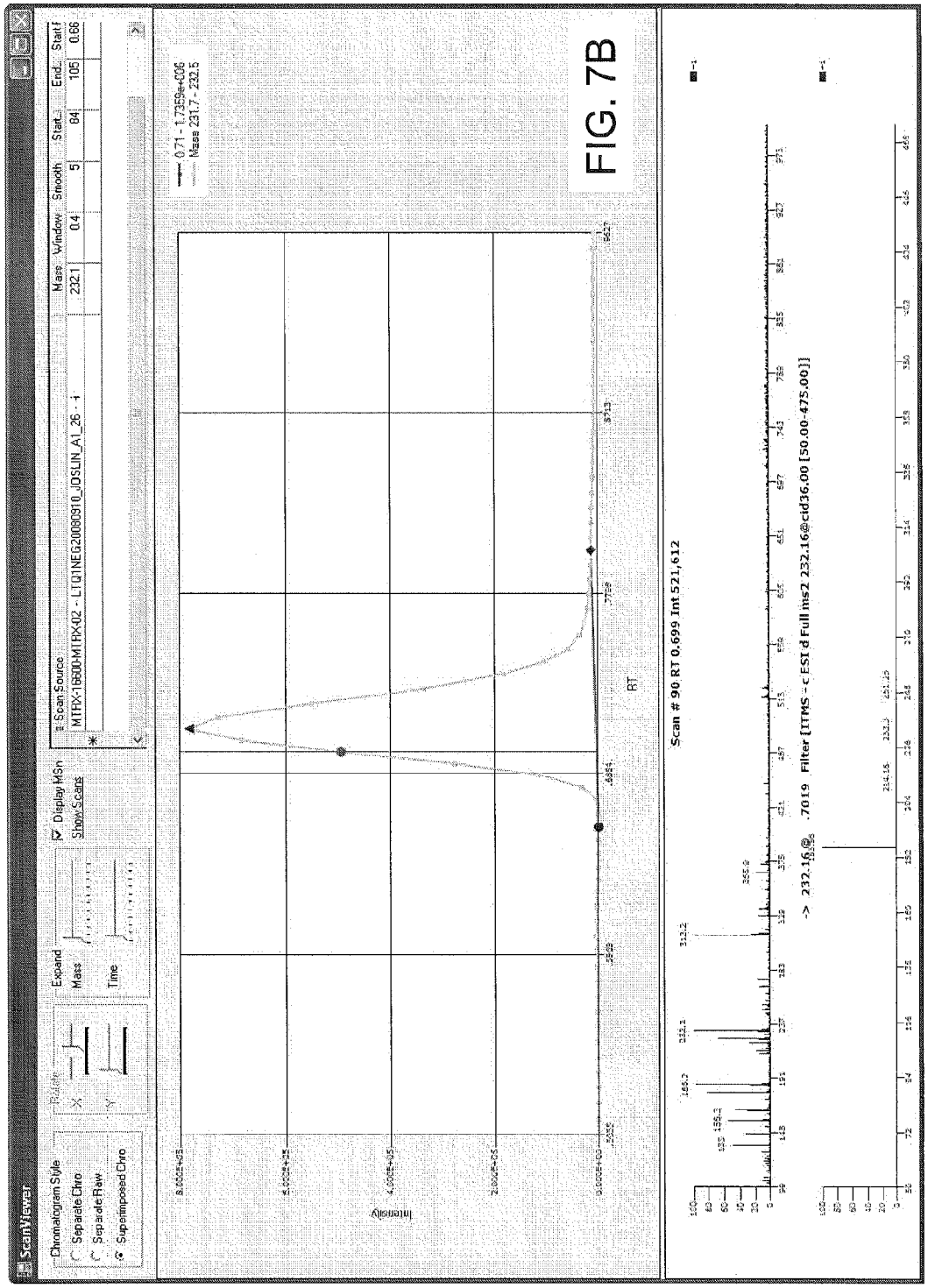
Figure 7C:
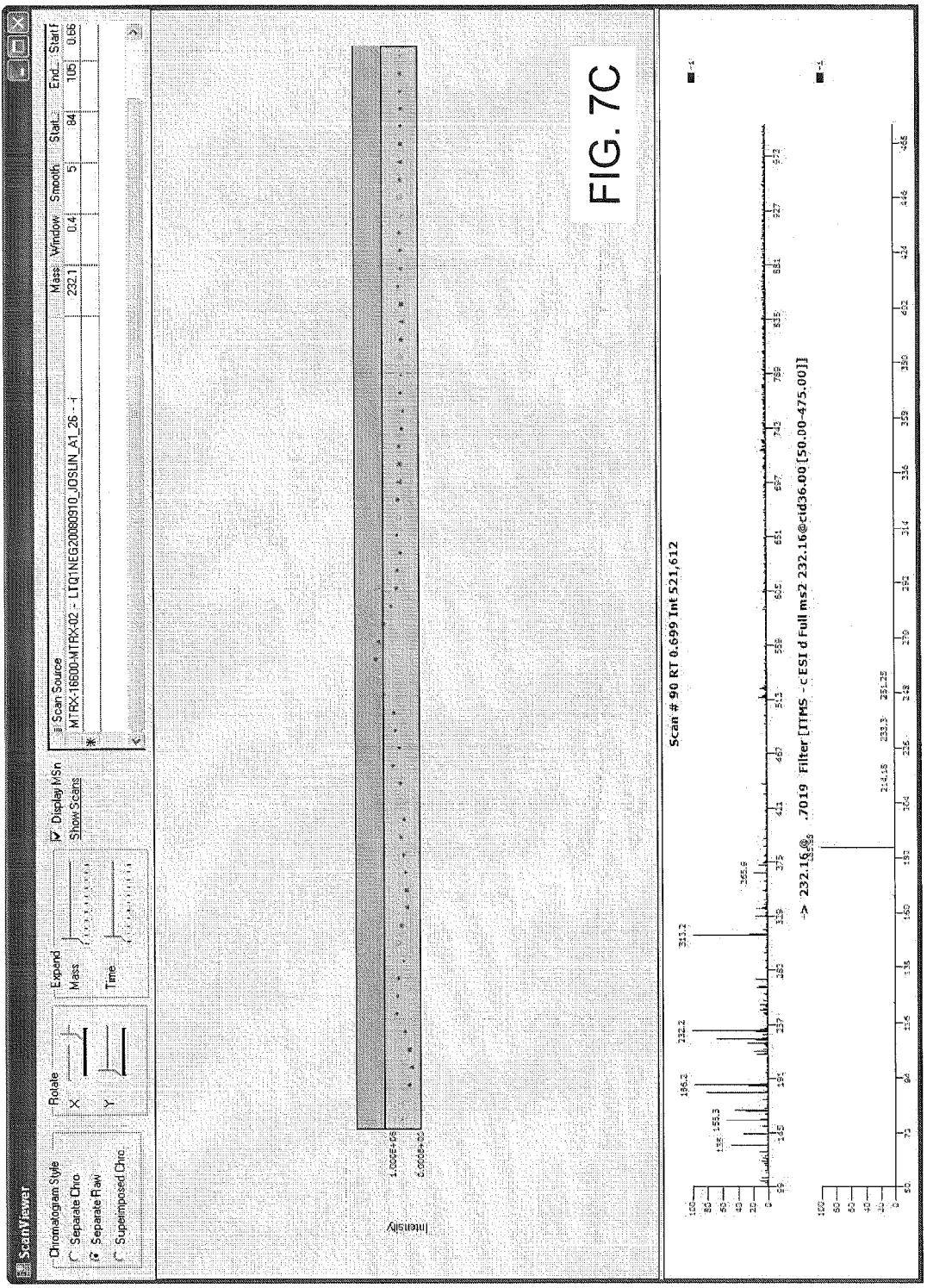
Figure 9:
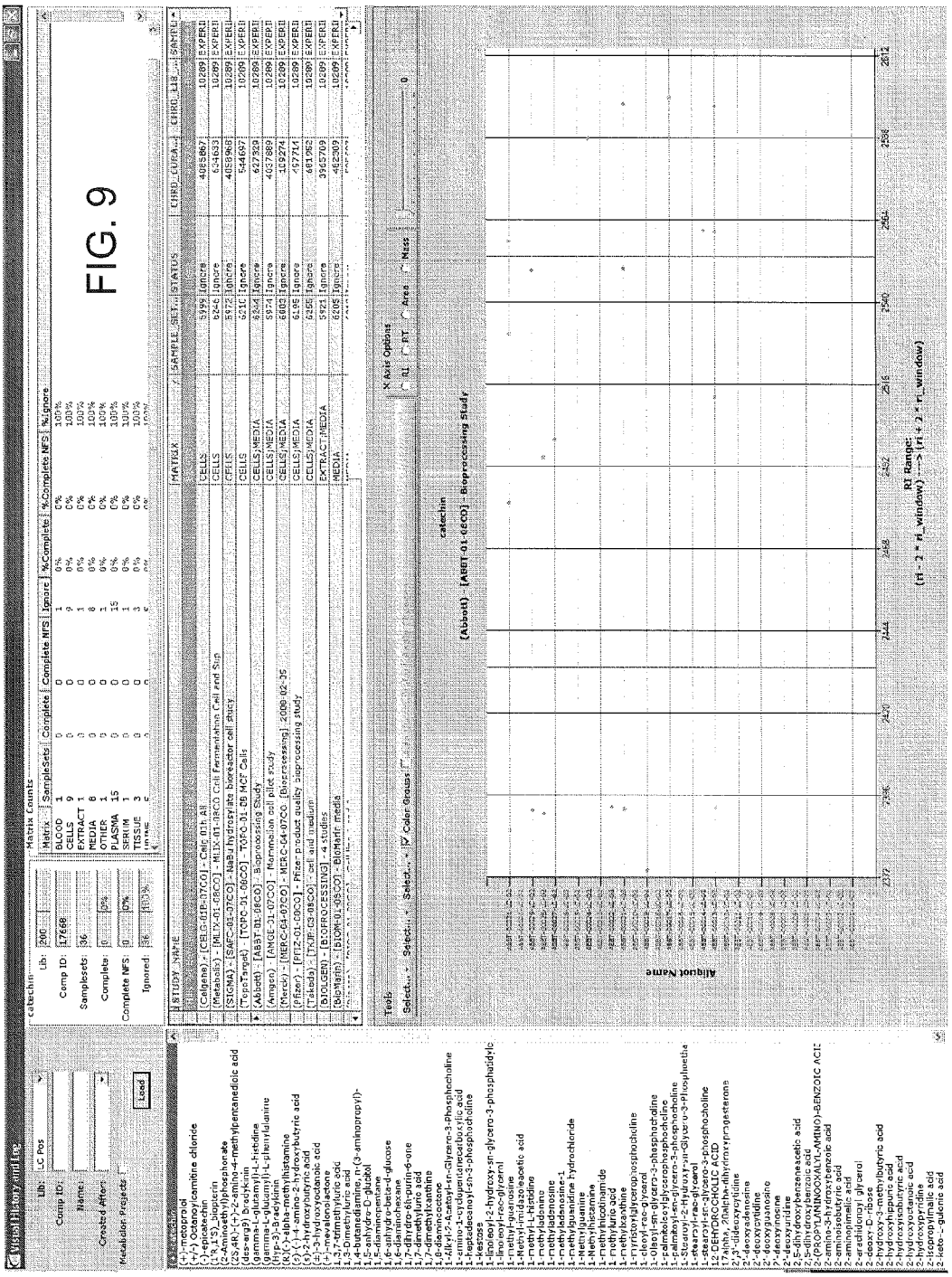
Figure 10:
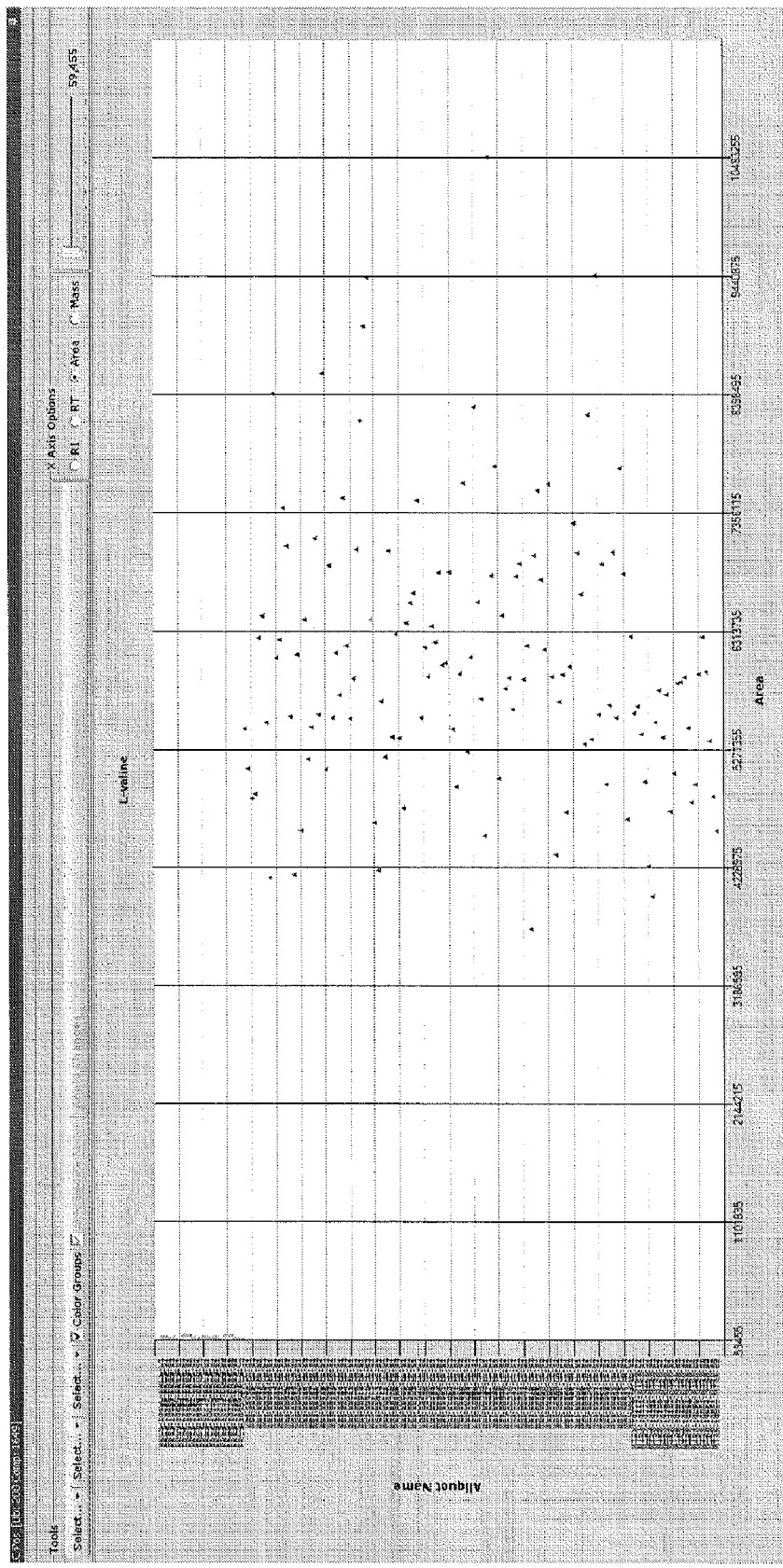

Having thus described the invention in general terms, reference will now be made to the accompanying drawings, which are not necessarily drawn to scale, and wherein:

FIG. 1 illustrates a system according to one embodiment of the present invention including a database, including a memory device and user interface, in communication with a spectrometry device;

FIG. 2a is an illustration of a three-dimensional plot of spectrometry data typically associated with one exemplary sample;

FIG. 2b is an illustration of a two-dimensional plot that may be generated by some embodiments of the system of the present invention that may be comparable to a plurality of characteristic plots corresponding to a plurality of selected metabolites;

FIG. 2c is an illustration of a plot that may be generated by some embodiments of the system of the present invention including a visual indication of the presence of the selected metabolites in each of a plurality of samples;

FIG. 3 is an illustration of the operation flow of the systems, methods, and computer program products according to one exemplary embodiment;

FIG. 4 is an illustration of a verification/confirmation process regarding the presence of selected metabolites in each of a plurality of samples, according to one embodiment of the present invention, involving post-analysis data obtained from various analytical devices, channels of a single analytical device, or combinations thereof;

FIG. 5 is an illustration of a verification/confirmation process regarding the presence of selected metabolites in each of a plurality of samples, according to one embodiment of the present invention, involving a direct comparison of post-analysis data obtained from different analytical devices, or different channels of a single analytical device, or combinations thereof;

FIG. 6 is an illustration of a verification/confirmation process regarding the presence of selected metabolites in each of a plurality of samples, according to one embodiment of the present invention, which involves sorting post analysis data with respect to at least one of an experimental factor, a sample factor, and a process factor, and designating each such factor with a different indicia such as color;

FIG. 7A is an illustration of a verification/confirmation process regarding the presence of selected metabolites in each of a plurality of samples, according to one embodiment of the present invention, which involves associating at least one related information source with each of the screened plurality of samples determined to have the at least one of the plurality of selected metabolites associated therewith;

FIGS. 7B and 7C are illustrations of a verification/confirmation process regarding the presence of selected metabolites in each of a plurality of samples, according to one embodiment of the present invention, which involves associating one of the screened plurality of samples determined to have the at least one of the plurality of selected metabolites associated therewith, with at least one related information source comprising originally-collected (raw) data;

FIG. 8 is an illustration of a verification/confirmation process regarding the presence of selected metabolites in each of a plurality of samples, according to one embodiment of the present invention, which involves relating metabolites and related chemicals and/or biochemicals according to a particular common pathway;

FIG. 9 is an illustration of a verification/confirmation process regarding the presence of selected metabolites in each of a plurality of samples, according to one embodiment of the present invention, which involves relating a particular selected metabolite identified as being present in a particular sample or sample population, to completed studies where the same selected metabolite may also have been identified as being present in the analyzed sample or sample population; and FIG. 10 is an illustration of a verification/confirmation process regarding the presence of selected metabolites in each of a plurality of samples, according to one embodiment of the present invention, which involves varying an axis parameter of a comparison across a plurality of the screened plurality of samples, so as to visually indicate an effect of a particular sample-related factor across the plurality of the screened plurality of samples.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The various aspects of the present invention mentioned above, as well as many other aspects of the invention, are described in greater detail below. The systems, methods, and computer program products of embodiments of the present invention are exemplarily disclosed in conjunction with an appropriate analytical device which may, in some instances, comprise a separator portion (i.e., a chromatograph) and a detector portion (i.e., a spectrometer). It must be understood that this is only one example of the implementation of embodiments of the present invention. Particularly, the systems, methods, and computer program products of embodiments of the present invention can be adapted to any number of processes that are used to generate complex sets of data across a plurality of samples, whether biological, chemical, or biochemical, in nature. For example, embodiments of the present invention may be used with a variety of different analytical devices and processes including, but not limited to: analytical devices including a separator portion comprising one of a liquid chromatograph (LC) and a gas chromatograph (GC); a cooperating detector portion comprising one of a nuclear magnetic resonance imaging (NMR) device; a mass spectrometer (MS); and an electrochemical array (EC); and/or combinations thereof. In this regard, one skilled in the art will appreciate that the embodiments and aspects of the present invention as disclosed herein are not limited to metabolomics analysis. For example, the embodiments and aspects of the present invention as disclosed herein can be can be implemented in other applications where there is a need to characterize the small molecules present within a sample, regardless of the origin of the sample. For instance, the embodiments and aspects of the present invention as disclosed herein can also be implemented in a bioprocess optimization procedure where the goal is to grow cells to produce drugs or additives, in a drug metabolite profiling procedure where the goal is to identify all metabolites that are the result of biotranformations of an administered xenobiotic. As will be appreciated by one skilled in the art, these exemplary applications may be very different from a metabolomics analysis, where the goal is only to examine endogenous metabolites. Some other non-limiting examples of other applications could include a quality assurance procedure for consumer product manufacturing where the goal may be to objectively ensure that desired product characteristics are met, in procedures where a large number of sample components can give rise to a particular attribute, such as taste or flavor (e.g., cheese, wine or beer), or scent/smell (e.g., fragrances). One common theme thus exhibited by the embodiments and aspects of the present invention as disclosed herein is that the small molecules in the sample can be determined using the various system, method and computer program product embodiments disclosed herein.

FIG. 1 illustrates an example of a system according to one embodiment of the present invention wherein the system is in communication with an analytical device 110, such as a combination chromatograph/mass spectrometer. One skilled in the art will appreciate, however, that the configurations of an analytical device 110 presented herein are for exemplary purposes only, and are not intended to be limiting with respect to the scope of suitable and appropriate analytical devices that may also be applied under the principles disclosed herein As shown, a sample (whether biological, chemical, or biochemical, in nature) 100 may be introduced into the separator portion of the analytical device 110 and analyzed using appropriate techniques, as applied through the detector portion, that will be appreciated by those skilled in the art. For example, the components of a particular sample 100 may pass through a column associated with the separator portion, at different rates and exhibit different spectral responses via the detector portion based upon their specific characteristics. As will be appreciated by one skilled in the art, the analytical device 110 may generate a three-dimensional set of spectrometry data corresponding to each sample 100, wherein the data included in the three-dimensional data set generally indicates the composition of the sample 100. However, such data must first be appropriately analyzed in order to determine the sample composition.

An example of such a three-dimensional set of spectrometry data is shown generally in FIG. 2a, and may be plotted on a three-axis plot, including axes for response intensity 220, component mass 210, and time 230 (particularly, in this example, the time a particular component spends in the column of the separator portion of the analytical device 110). The location of data points relative to the component mass axis 210 may be indicative, for example, of the number of individual component molecules within the sample 100 and the relative mass values for such components. According to other embodiments of the system of the present invention, alternate analytical devices may be used to generate a three-dimensional set of analytical data corresponding to the sample 100. For example, the analytical device may include, but is not limited to: various combinations of a separator portion comprising one of a liquid chromatograph (LC) and a gas chromatograph (GC); and a cooperating detector portion comprising one of a nuclear magnetic resonance imaging (NMR) device; a mass spectrometer (MS); and an electrochemical array (EC). One skilled in the art will appreciate that such complex three-dimensional data sets may be generated by other appropriate analytical devices that may be in communication with components of the system embodiments of the present invention as described in further detail below.

A plurality of samples 100 may be taken individually from a well plate 120 and/or from other types of sample containers and introduced individually into the analytical device 110 for analysis and generation of the corresponding three-dimensional data set (see, e.g., FIG. 2a). For example, individual samples 100 may be transferred from a well plate 120 to the analytical device 110 via pipette, syringe, microfluidic passageways defined by a test array, and/or other systems for transferring samples in a laboratory environment. The samples may include, but are not limited to: blood samples, urine samples, cell cultures, saliva samples, and/or other types of biological, chemical, and/or biochemical samples in which the metabolites and/or chemical components of interest may be present.

As shown in FIG. 1, the system embodiments of the present invention may comprise a database (e.g., a relational database) stored, for example, in a memory device 140, wherein the database is in communication with a processor device 130 (e.g., a computer device), wherein the database (memory device 140) and/or the processor device 130 may be configured to be in communication with the analytical device 110 for automatically receiving a three-dimensional data set, corresponding to each of the plurality of samples 100, therefrom. The processor device 130 may be in communication with the analytical device 110 via wire (RS-232, and/or other types of wire connection) and/or wireless (such as, for example, RF, IR, or other wireless communication) techniques such that the database associated with the memory device 140/processor device 130 (and/or in communication therewith) may receive the data set from the analytical device 110 so as to be stored thereby Furthermore, the analytical device 110 may be in communication with one or more processor devices 130 (and associated user interfaces 150) via a wired and/or wireless computer network including, but not limited to: the Internet, local area networks (LAN), wide area networks (WAN), or other networking types and/or techniques that will be appreciated by one skilled in the art. The database may be structured using commercially-available software, such as, for example, Oracle, Sybase, DB2, or other database software. As shown in FIG. 1, the processor device 130 may be in further communication with the memory device 140 (such as a hard drive, memory chip, flash memory, RAM module, ROM module, and/or other memory device 140) for storing the database, including the three-dimensional data sets automatically received from the analytical device 110. In addition, the memory device 140 may also be used to store other data received by the database and/or otherwise manipulated by the processor device 130.

The processor device 130 may, in some embodiments, be capable of converting each of the three dimensional data sets (see FIG. 2a) received by the database 140 into at least one corresponding two-dimensional data set (see FIG. 2b), wherein the at least one two-dimensional data set comprises, for example, a two-dimensional "profile" of a particular sample 100 at a particular point 235 along the time axis (wherein time is measured from a zero point, when the sample 100 is injected and/or otherwise introduced into the analytical device 110). For example, the processor device may produce a mass versus intensity profile of the sample at a given time point 235 (see FIG. 2b, for example). The "x" axis (or time axis 230, for example) may further be characterized as a retention index and/or a retention time. Thus, the processor device 130 may be further capable of parsing each of the three-dimensional data sets into one or more individual two-dimensional profiles corresponding to particular points (235, for example) in time so as to convert each three-dimensional data set (of FIG. 2a, for example) into at least one corresponding two-dimensional data set (having a profile shown, for example, in FIG. 2b) that may further be plotted as an intensity response 220 versus mass 210.

Furthermore, according to some system embodiments, the processor device 130 (in communication with the database) may be further configured to systematically compare each of the at least one plotted two-dimensional data set (as shown, for example, in FIG. 2b) to a plurality of characteristic plots corresponding to a plurality of selected metabolites so as to screen the plurality of samples 100 for a presence of at least one of the plurality of selected metabolites. As will be appreciated by one skilled in the art, selected known and/or known but "unnamed" metabolites may exhibit characteristic mass vs. intensity profiles in association with a characteristic retention time with respect to the separator portion of the analytical device 110. Specifically, in some embodiments, the processor device 130 may comprise and/or be in communication with the memory device 140 for storing the plurality of characteristic plots corresponding to the selected metabolites (i.e., in a "library" or repository of such characteristic plots). For example, one skilled in the art will appreciate that metabolites may be identified with varying degrees of certainty (e.g., confidence) by comparing a two-dimensional plot of response intensity (sometimes expressed in $\mu A$ (as shown in FIG. 2b) resulting from a mass spectrometry analysis with stored two-dimensional profiles corresponding to selected metabolites, for instance, through a "peak matching" procedure. Thus, embodiments of the present invention may be capable of systematically comparing each of the at least one plotted two-dimensional data sets (correspond, for example, to each sample 100) to a series of characteristic plots corresponding to selected metabolites, in order to facilitate an identification thereof. It should be understood that the various system and method embodiments of the present invention may be capable of comparing each of the at least one plotted two-dimensional data sets to a series of characteristic plots corresponding to selected metabolites, wherein the characteristic plots may correspond to "known named" and/or "known, but unnamed" chemicals/compounds. For example, embodiments of the present invention are capable of utilizing characteristic plots (stored in a memory device 140, for example) that correspond both to metabolites having chemical names and/or those "known, but unnamed" metabolites for which characteristic plots have been identified, but for which a chemical name and/or classification has not yet been assigned. Further, for the screened plurality of samples determined to have the at least one of the plurality of selected metabolites associated therewith, the processor device 130 may be further configured to compare the at least one plotted two-dimensional data set for each of the screened plurality of samples may (i.e., with respect to each other), across the screened plurality of samples, so as to determine a trend or other relationship of the associated at least one of the plurality of selected metabolites, across the screened plurality of samples.

Furthermore, because the database of the present invention is capable of storing metabolomic data from a plurality samples 100, in a single relational database, sample 100 data (specifically profile data corresponding to certain selected time points) can be readily determined and/or compared, such that the certainty of or confidence in a "match" between the at least one plotted two-dimensional data set and one of the characteristic plots of selected metabolites (or other chemicals) may be used to infer the presence of a selected metabolite in a sample 100, in instances when there may be a less-than-certain profile match. Thus, a user of system embodiments of the present invention may be able to subjectively (or, in other instances, at least partially objectively) determine that a plotted two-dimensional data set that may, for example, fail to meet a minimum threshold for a "certain" identification, may actually be indicative of the presence of a selected metabolite, given a prevalence of certain correlations among the corresponding plotted two-dimensional data sets across an overall population of samples 100. Embodiments of the present invention may thus utilize a visual indication of sufficiently "certain" matches (i.e., with sufficient confidence) across a population of samples 100 (as shown in FIG. 2c, for example) to infer that uncertain, but likely matches are, in fact, valid data points and indicative of a "match" that, in turn, indicates the presence of a selected metabolite and/or chemical component in the sample 100.

For example, the profile shown in FIG. 2b, in the case of some samples 100, may match a characteristic plot of a selected metabolite (such as a known metabolite and/or a known, but unnamed metabolite, for example) with sufficient certainty (which may be shown as a data point within a selected time frame 260, 270, as shown in FIG. 2c, wherein the data point may represent, for example, an intensity peak in the corresponding two-dimensional data set). However, due to variations in samples, potential contaminants within samples 100, and/or other experimental factors that will be appreciated by those skilled in the art, some three-dimensional data sets generated by the analysis of some samples 100 may result in corresponding two-dimensional mass versus response intensity profiles at a given time that may not match a characteristic plot with such sufficient certainty. In existing "file-based" data analysis systems, each sample 100 is analyzed individually such that the presence of certain metabolites or other chemicals may be unduly and/or prematurely discounted due to the fact that the two-dimensional data set (and corresponding profile plot (as shown in FIG. 2b)) is not capable of being subjectively analyzed in light of an associated population of samples 100 (i.e., as a measure of consistency in the identification of the particular metabolite(s)).

Embodiments of the system of the present invention, may further comprise a user interface 150 in communication with said processor device 130/memory device 140 for displaying a visual indication 160 (see also, FIG. 2c, for example) of the presence of the selected metabolite(s) (as indicated by intensity peaks and certain metabolite "matches") across the plurality of samples 100 on a time axis 240 that is indicative of the time at which selected intensity peaks were determined from the data detected by the analytical device 110. The user interface 150 may be capable of displaying to the user, for example, a display 160 of sample number 250 (indicating the identity of the sample 100) versus time 240, as shown generally in FIG. 2c. More particularly, in some system embodiments, the user interface 150, in communication with the database/processor device 130, may be configured to display a visual indication of the comparison of the at least one plotted two-dimensional data set for each of the screened plurality of samples, across a plurality of the screened plurality of samples, to visually indicate the screened plurality of samples determined to have the at least one of the plurality of selected metabolites associated therewith, and the trend or other relationship corresponding thereto, across the plurality of the screened plurality of samples.

The user interface 150 may comprise, for example, a display device, personal computer, and/or other electronic device having a display for graphical representation of data. For example, as shown in FIG. 2c, a graphical plot of time 240 versus sample number 250 may be generated by the database/processor device 130 and displayed via the user interface 150 such that differences in the component makeup of each sample and/or the differences between samples in an overall population of samples 100 may be visually discernable by a user of the system embodiments of the present invention. In some embodiments, the user interface 150 and/or processor device 130 may be capable of generating time threshold markers 260, 270 so that a user may specify visual boundaries on the display 160 (FIG. 2c) in order to readily identify outlying data associated with some samples (for example, Sample #7 as shown in FIG. 2c) that may fail to exhibit intensity peaks falling within the selected time frame (as defined by time thresholds 260, 270), and thus may not provide a sufficient "match." Thus, a user of the system of the present invention may utilize the multi-sample visual depiction of FIG. 2c to discern a specific time 265 about which intensity peaks were detected in the majority of samples 100 displayed on the display 160. The system embodiments of the present invention may then call up or otherwise access specific profile plots for certain metabolites (see FIG. 2b, for example) corresponding to the specific time 265, and then compare profile plots to any of the two-dimensional plots of any of the samples shown in FIG. 2c, such that a user may then subjectively determine if one of the profile plots (of mass 210 vs. intensity 220) indicates that the selected sample does indeed indicate the presence of the corresponding selected metabolite (which may be indicated, for example, by a less-than-optimal intensity peak for a given characteristic mass).

Furthermore, as shown in FIG. 2c, the system embodiments of the present invention may also allow a user to compile and display multiple time thresholds 260, 270 during which peak intensities were objectively determined (by a user and/or system-defined threshold) for each of the samples 250. That is, FIG. 2c represents, for example, the location of certain intensity peaks, as they relate to the multiple time thresholds 260, 270, across the plotted two-dimensional data sets for each of the samples 250. As such, the analysis results are displayed to a user in a compact format that spans a "fourth dimension" across the population of samples. This displayed information may further add to evidence that may be utilized by a user to make the subjective decision to accept a "less than certain" profile match as an indication of the presence of a selected metabolite. For example, as described above, and shown in FIG. 2c, no objective intensity peak for Sample #7 was detected by the analytical device 110 at time t1, or was otherwise not evident in the two-dimensional data set for that sample. However, objective intensity peaks were ostensibly detected in all other samples shown in this example. Thus, the processor device 130 may detect this aberration and automatically display the two-dimensional profile information (see FIG. 2b) to a user, via the user interface, for Sample #7 at time t1, such that a subjective user decision may be made (i.e., match or no match) with respect to the analytical device 110 objective determination. Furthermore, the system embodiment of the present invention may also allow a user to further confirm the subjective determination of the presence of an obscured and/or otherwise undetected peak at t1 (e.g., for Sample #7) by displaying (in the time 240 versus sample 250 plot format of FIG. 2c) the presence of an objective intensity "peak" at time t2 for further comparison.

System embodiments of the present invention may thus allow a user to quickly discern which samples 100 (displayed on a time plot 160, via a user interface 150) may require further subjective scrutiny. Furthermore, using the time threshold markers 260, 270 in conjunction with the display 160 of the entire population of sample 100 results, the processor device 130 of the present invention may then automatically identify and retrieve (from the memory device 140 and/or database 130) the series of at least one two-dimensional plots (see FIG. 2b) corresponding to the samples 100 that may not exhibit a sufficient "match" or characteristic intensity peaks at the selected times 265 when compared to the overall population of samples. The two-dimensional plots retrieved from the database (i.e., corresponding to the samples exhibiting the outlying points 280) may then be subjectively analyzed to determine if the absence of a characteristic peak at the selected time 265 is indicative of a lack and/or presence of selected metabolites that may differ from the chemical composition of the majority of the analyzed population of samples 100.

Some system embodiments may thus generate a listing or other indicia of one or more metabolites present in the samples, from the overall population of samples 100, on the graphical display 150 as shown, for example, in FIG. 2c. The listing of identified metabolites may thus provide, for example, a corresponding list of disease targets for pharmaceutical development or other therapy. In addition, in some embodiments, the processor device 130, in cooperation with the database, may also be used to map clinical data including, but not limited to: symptoms exhibited by patients from whom the samples 100 have been taken; known disease states of the patients from whom the samples 100 have been taken; patient physiological data; other supplemental patient data (height, weight, age, etc.); and/or other clinical data. Thus, using the database of the present invention, other clinical/experimental factors may be correlated with the identified presence of selected metabolites in one or more samples 100 such that the database/processor device 130 may be used to generate predictive tests for diseases and/or disorders that may exhibit characteristic and measurable changes in metabolomic data.

Embodiments of the present invention also provide a method for compiling and comparing (i.e., analyzing) metabolomics data across a plurality of samples 100, as shown generally in the flow diagram of FIG. 3. Step 310 comprises automatically receiving a three-dimensional data set (such as that shown graphically in FIG. 2a) corresponding to each of the plurality of samples 100 in a database. As shown generally in FIG. 1, and as described above, the three-dimensional data set may comprise spectrometry data received by the database/processor device 130 which may be in communication (via wired and/or wireless connection) with a processor device 130 (such as a computer device) and an analytical device 110 (i.e., a chromatograph/mass spectrometer) capable of generating analytical data corresponding to a sample 100 containing a plurality of metabolites and other chemical components. In some embodiments, wherein the three-dimensional data set is generated by and received from a mass spectrometer, the axes defining the three-dimensional data set may comprise, as shown generally in FIG. 2a: component mass 210, response intensity 220, and time 230 (wherein time refers to the time a particular component of the sample 100 is retained in the column of the spectrometer 110). Furthermore, the automatic receiving step 310 may be repeated for a number of samples 100 in a defined population of samples, wherein the resulting data is automatically compiled by the processor device 130 of the present invention such that analytical data corresponding to each sample 100 is indexed and remains selectively retrievable from the database by the processor device 130 (and/or a computer device or user interface 150 in communication therewith).

More specifically, in some method embodiments, the automatic receiving step 310 may further comprise: compiling the three-dimensional data associated with a plurality of samples 100 in order to generate a population data set (that may be used to further determine, for example, statistical boundaries of the sample population); and indexing the three-dimensional data according to the individual sample 100 such that, as statistical outliers (see Sample #7 at FIG. 2c, for example) among the samples 100 are identified relative to the overall population of samples, the data corresponding to the particular "statistical outlier" samples 100 (i.e., Sample #7) may be retrieved from the database by the processor device 130 and displayed to a user (e.g., via a user interface 150), for instance, as a two-dimensional plot, for a subjective determination of whether one or more selected metabolites are present in those samples 100. As described above, the system embodiments of the present invention may be used to define time thresholds (see elements 260, 270 of FIG. 2c) such that the database/processor device 130 may retrieve data corresponding to samples 100 exhibiting a selected variance with respect to those time thresholds, from the sample population.

Step 320 of the method embodiments of the present invention comprises converting each three-dimensional data set (shown generally in FIG. 2a) into at least one corresponding two-dimensional data set (shown generally in FIG. 2b). Step 320 may comprise, for example, parsing the three-dimensional data set along the time axis 220 such that each component of the sample 100 having a different retention time may be associated with a corresponding two-dimensional data set plotted as response intensity 220 versus mass 210 (e.g., see FIG. 2b). Method embodiments of the present invention may also comprise Step 330 for plotting the at least one two-dimensional data set, as shown in FIG. 2b, for each of the plurality of samples. For example, in method embodiments wherein spectrometry data is automatically received by the database in step 310, step 330 may comprise plotting each two-dimensional data set (corresponding to a sample 100 component having characteristic retention time within a spectrometer column, for example) relative to mass 210 and response intensity 220 axes that may be directly comparable to characteristic plots of selected metabolites. Thus, method step 340 comprises comparing the at least one plotted two-dimensional data set (see FIG. 2b, for example) to a plurality of characteristic plots corresponding to a plurality of selected metabolites so as to screen the plurality of samples 100 by associating at least one of the plurality of selected metabolites with the at least one plotted two-dimensional data set for each of the plurality of samples.

One skilled in the art will appreciate that such two-dimensional profiles may be indicative of the presence and/or absence of a particular metabolite and/or other chemical component within a sample 100 as analyzed by the mass spectrometer. However, one skilled in the art will also appreciate that only a certain amount of samples may produce mass versus response intensity profiles that indicate a certain or definite match with a selected metabolite. Method embodiments of the present invention may thus also comprise step 330 for plotting the at least one two-dimensional data set (corresponding to a sample 100 component having a particular mass, for example), as shown in FIG. 2b, for each of the plurality of samples, relative to time 230 and response intensity 220 axes that may be directly comparable to characteristic plots of selected metabolites. Thus, method step 340 comprises comparing the at least one plotted two-dimensional data set (see FIG. 2b, for example) to a plurality of characteristic plots corresponding to a plurality of selected metabolites so as to screen the plurality of samples 100 for a presence of at least one of the plurality of selected metabolites. As described herein with respect to the various system embodiments of the present invention, it should be understood that the method embodiments may also be capable of comparing each of the at least one plotted two-dimensional data sets to a series of characteristic plots corresponding to selected metabolites that may include, but are not limited to: "known and named metabolites," and/or "known, but unnamed" metabolites. For example, various method embodiments described herein are capable of utilizing characteristic plots that correspond both to metabolites having chemical names and/or those "known, but unnamed" metabolites for which characteristic plots have been identified, but for which a chemical name and/or classification has not yet been assigned.

For the screened plurality of samples determined to have the at least one of the plurality of selected metabolites associated therewith, the at least one plotted two-dimensional data set for each of the screened plurality of samples may then be compared (i.e., with respect to each other), across the screened plurality of samples, so as to determine a trend or other relationship of the associated at least one of the plurality of selected metabolites, across the screened plurality of samples.

As shown in FIG. 3, Step 350 comprises displaying a visual indication of the comparison of the at least one plotted two-dimensional data set for each of the screened plurality of samples, across a plurality of the screened plurality of samples, to visually indicate the screened plurality of samples determined to have the at least one of the plurality of selected metabolites associated therewith, and any trend corresponding thereto, across the plurality of the screened plurality of samples 100 (i.e., in a "fourth dimension" across the plurality of samples). According to some embodiments, this method step may further comprise: generating a graphical display (as shown, for example, in FIG. 2c) of time 240 (i.e., time of detection of an objective matching intensity "peak") versus sample number 250 to first facilitate identification of samples 100 having a lack of characteristic peaks within a selected time period (as defined by, for example, time thresholds 260, 270) when compared to the overall associated sample population; and retrieving the at least one two-dimensional data set corresponding to the samples 100 exhibiting a lack of characteristic peak(s) in response to such identification such that a user may make a subjective determination of the presence or absence of a selected metabolite and/or chemical component. Finally, step 350, may, in some embodiments, further comprise providing a listing or other indicia of metabolites and/or chemical components that are present in the analyzed samples 100.

Thus, the method embodiments of the present invention may allow for the subjective determination of the presence and/or absence of a selected metabolite and/or chemical component within a sample 100 by linking data from an associated population of samples in a database such that, as characteristic data sets (i.e., as plotted in FIG. 2b) are accumulated for each sample, the data sets may be linked and further utilized to map characteristic data across the plurality of samples 100 (as plotted, for example, in FIG. 2c). The visual indication of FIG. 2c may thus allow for the ready identification of specific samples that may require further subjective scrutiny. This may be especially apparent, for example, in FIG. 2c, when a particular sample does not exhibit characteristic peaks and/or profile matches at each time of interest 265, but does conform to the overall population data in other respects. While previous data analysis methods may have discounted and/or discarded such samples 100, the method of embodiments of the present invention allows a user to highlight such samples for closer subjective scrutiny, such that the aberrations may be either explained and/or determined to be indicative of a fundamental chemical difference of the particular sample with respect to the associated population of samples.

Another aspect of the present invention is directed to the verification or confirmation of the identification (or lack of identification) of the at least one selected metabolite determined to be commonly associated with the plurality of samples comprising the analyzed population of samples. For example, inconsistent analysis results may, in some instances, be obtained from verification studies due to, for instance, variations between analytical devices, or even variations between channels of a single analytical device. In another respect, particular analytical devices, or even particular channels of a single analytical device, may be known to have certain characteristics reflected in the analytical data obtained therefrom. Accordingly, if various analytical devices have quantifiable or otherwise known characteristics/behaviors, the analysis of the sample population according to method embodiments disclosed herein, can be extended to encompass data acquired from more than one analytical device, or more than one channel of a single analytical device, or combinations thereof (see, e.g., FIG. 4, elements 410, 420, and 430 which represents sample data obtained, for example, from samples exposed to a separator portion of the analytical device comprising one of the positive channel of a liquid chromatograph, a gas chromatograph, and the negative channel of a liquid chromatograph, respectively), for verifying or otherwise confirming the analysis results for the subject population of samples. In some instances, this analysis verification/confirmation principle may further be extended to include an analysis of data associated with different retention/detection times for a single analytical device (see, e.g., FIG. 4, elements 400 and 420 which represent sample data obtained, for example, at different retention times 440, 450 in separator portion comprising a gas chromatograph, possibly the same gas chromatograph), or single channel of a certain analytical device, as previously disclosed.

More particularly, such a method of analyzing metabolomics data, and a computer program product embodying such a method, comprises automatically receiving a three-dimensional data set of metabolomics data, corresponding to each of a plurality of samples, in a database from each of a first data source 110 (see, e.g., FIG. 1) and a second data source 115 (see, e.g., FIG. 1). Each data source may comprise, for example, a different analytical device (i.e., various combinations of a separator portion comprising one of a liquid chromatograph (LC) and a gas chromatograph (GC); and a cooperating detector portion comprising one of a nuclear magnetic resonance imaging (NMR) device; a mass spectrometer (MS); and an electrochemical array (EC)), different channels of a separator portion of a single analytical device (i.e., a positive channel and a negative channel of a liquid chromatograph), or combinations thereof. For the metabolomics data from each of the first and second data sources 110, 115, the three-dimensional data set (see, e.g., FIG. 2a) is converted into at least one corresponding two-dimensional data set (see, e.g., FIG. 2b) for each of the plurality of samples, and the at least one two-dimensional data set for each of the plurality of samples is plotted. The at least one plotted two-dimensional data set for each of the plurality of samples is compared to a plurality of characteristic plots corresponding to a plurality of selected metabolites so as to screen the plurality of samples by associating at least one of the plurality of selected metabolites with the at least one plotted two-dimensional data set for each of the plurality of samples. For the screened plurality of samples determined to have the at least one of the plurality of selected metabolites associated therewith, the at least one plotted two-dimensional data set for each of the screened plurality of samples is compared, across the screened plurality of samples, so as to determine a trend of the associated at least one of the plurality of selected metabolites, across the screened plurality of samples. A visual indication of the comparison of the at least one plotted two-dimensional data set for each of the screened plurality of samples, across a plurality of the screened plurality of samples, is then displayed (see, e.g., FIG. 2c) to visually indicate the screened plurality of samples determined to have the at least one of the plurality of selected metabolites associated therewith, and the trend corresponding thereto, across the plurality of the screened plurality of samples, for the metabolomics data from each of the first and second data sources. The first and second data sources are then compared with respect to the at least one of the plurality of selected metabolites determined to be included in the metabolomics data (see, .e.g., FIG. 4), and the trend across the screened plurality of samples associated therewith (see, .e.g., FIG. 5), so as to determine an identity confidence measure associated with the at least one of the plurality of selected metabolites.

Similarly, an associated apparatus/system embodying the disclosed analysis verification/confirmation principle for analyzing metabolomics data, comprises a database in communication with each of the first data source 110 and the second data source 115, as previously disclosed, wherein the database is configured to automatically receive a three-dimensional data set of metabolomics data corresponding to each of a plurality of samples, from each of the first and second data sources 110, 115. A processor device 130 is in communication with the database, wherein the processor device 130 is configured, for the metabolomics data from each of the first and second data sources 110, 115, to convert the three-dimensional data set into at least one corresponding two-dimensional data set for each of the plurality of samples; plot the at least one two-dimensional data set for each of the plurality of samples; compare the at least one plotted two-dimensional data set for each of the plurality of samples to a plurality of characteristic plots corresponding to a plurality of selected metabolites so as to screen the plurality of samples by associating at least one of the plurality of selected metabolites with the at least one plotted two-dimensional data set for each of the plurality of samples; and compare, for the screened plurality of samples determined to have the at least one of the plurality of selected metabolites associated therewith, the at least one plotted two-dimensional data set for each of the screened plurality of samples, across the screened plurality of samples, so as to determine a trend of the associated at least one of the plurality of selected metabolites, across the screened plurality of samples. A user interface 150 (see, e.g., FIG. 1) is in communication with the database and the processor device 130, wherein the user interface 150 is configured to display a visual indication of the comparison of the at least one plotted two-dimensional data set for each of the screened plurality of samples, across a plurality of the screened plurality of samples, to visually indicate the screened plurality of samples determined to have the at least one of the plurality of selected metabolites associated therewith, and the trend corresponding thereto, across the plurality of the screened plurality of samples, for the metabolomics data from each of the first and second data sources 110, 115. The displayed visual indication is further configured to facilitate determination of an identity confidence measure associated with the at least one of the plurality of selected metabolites from a comparison of the first and second data sources 110, 115 with respect to the at least one of the plurality of selected metabolites determined to be included in the metabolomics data and the trend across the screened plurality of samples associated therewith. In some instances, as shown in FIG. 5 (comparing data from the positive and negative channels 500, 510 of a liquid chromatograph), the comparison of the first and second data sources 110, 115 with respect to the at least one of the plurality of selected metabolites determined to be included in the metabolomics data and the trend across the screened plurality of samples associated therewith, may be displayed together on a single plot, wherein this correlation of the responses of various analytical devices, channels of a single analytical device, or combinations thereof, facilitates an evaluation of the confidence or certainty of the identification of the one or more selected metabolites.

Yet another aspect of the present invention is directed to facilitating access to information regarding the at least one of the plurality of selected metabolites determined to be included in the metabolomics data and the trend across the screened plurality of samples associated therewith, in part to further the confirmation of, or otherwise verify, the identification and determination thereof. For example, one method of further facilitating the analysis of the data received from the analytical device(s) interacting with the sample(s) is to associate appropriate experimental factors, sample factors, process factors, other relevant factors, or combinations thereof, with each three-dimensional data set received by the database and corresponding to a respective one of the plurality of samples. By associating such relevant factors with the data, upon the data being collected by the analytical device(s), the post-analysis data may be further examined with respect to the associated factors in order to determine, for example, if one or more of such factors may have affected the collected data, and thus possibly affected the results of the analysis itself (i.e., the identification of the one or more selected metabolites).

More particularly, such a method of analyzing metabolomics data, and a computer program product embodying such a method, comprises automatically receiving a three-dimensional data set corresponding to each of a plurality of samples in a database, wherein each of the three-dimensional data sets has at least one of an experimental factor, a sample factor, and a process factor associated therewith. An experimental factor may include, for example, the age or sex of the subject from whom the sample was obtained, whether the subject was diseased, etc. A sample factor may include, for example, the conditions under which the sample was prepared, the chain of custody of the sample, etc. A process factor may include, for example, the run order of the sample through the analytical device, characteristics of the particular analytical device, sample batch data, etc. One skilled in the art, however, will appreciate that the terms "experimental factor," "sample factor," and "process factor" are only examples of the various factors that may appropriately be associated with the collected data, and which may be useful in further examining the post-analysis data. As such, these terms and the inclusion thereof in the specifications and the claims of the present invention are not intended to be limiting with respect to the scope of the "factors" that may be associated with the collected data in this manner.

The three-dimensional data set (see, e.g., FIG. 2a) is then converted by the processor device 130 into at least one corresponding two-dimensional data set for each of the plurality of samples, such that the respective at least one of an experimental factor, a sample factor, and a process factor remains associated with the corresponding two-dimensional data set. The at least one two-dimensional data set is plotted for each of the plurality of samples (see, e.g., FIG. 2b). The at least one plotted two-dimensional data set for each of the plurality of samples is then compared (e.g., by the processor device 130 in FIG. 1) to a plurality of characteristic plots corresponding to a plurality of selected metabolites so as to screen the plurality of samples by associating at least one of the plurality of selected metabolites with the at least one plotted two-dimensional data set for each of the plurality of samples. For the screened plurality of samples determined to have the at least one of the plurality of selected metabolites associated therewith, the at least one plotted two-dimensional data set for each of the screened plurality of samples is compared, across the screened plurality of samples, so as to determine a trend of the associated at least one of the plurality of selected metabolites, across the screened plurality of samples. A visual indication of the comparison (e.g., as displayed on a user interface 150 in FIG. 1) of the at least one plotted two-dimensional data set for each of the screened plurality of samples is compared, across a plurality of the screened plurality of samples, to visually indicate the screened plurality of samples determined to have the at least one of the plurality of selected metabolites associated therewith, and the trend corresponding thereto, across the plurality of the screened plurality of samples (see, e.g., FIG. 2c). The comparison of the at least one plotted two-dimensional data set for each of the screened plurality of samples displayed on the user interface 130 is then sorted, across a plurality of the screened plurality of samples, by the at least one of an experimental factor, a sample factor, and a process factor associated with the corresponding two-dimensional data set, so as to visually indicate the screened plurality of samples determined to have the at least one of the plurality of selected metabolites associated therewith, and the trend corresponding thereto, across the plurality of the screened plurality of samples, in relation to the at least one of an experimental factor, a sample factor, and a process factor (see, e.g., FIG. 6). In one instance, as shown in FIG. 6, each of the at least one of an experimental factor, a sample factor, and a process factor may be designated with a different color (see, e.g., elements 600-640) according to which the comparison may be further sorted. The factors of interest may be selected, for example, a "drop-down" menu 650 associated with the display of the comparison. As such, upon further sorting of the comparison, any effect of a particular factor of interest on the displayed post-analysis data may be visually discerned through, for instance, the color associated with the particular factor and the location of relevant data with respect thereto (i.e., factor 630 in FIG. 6 would appear to be relevant to the post-analysis data) as implemented through cooperation between the processor device 130 and the user interface 150.

Similarly, an associated apparatus/system embodying the disclosed further verification/confirmation principle for analyzing metabolomics data, comprises a database configured to automatically receive a three-dimensional data set of metabolomics data corresponding to each of a plurality of samples, wherein each of the three-dimensional data sets has at least one of an experimental factor, a sample factor, and a process factor associated therewith. A processor device 130 (see, e.g., FIG. 1) is in communication with the database, wherein the processor device 130 is configured to convert the three-dimensional data set into at least one corresponding two-dimensional data set for each of the plurality of samples, such that the respective at least one of an experimental factor, a sample factor, and a process factor remains associated with the corresponding two-dimensional data set; plot the at least one two-dimensional data set for each of the plurality of samples; compare the at least one plotted two-dimensional data set for each of the plurality of samples to a plurality of characteristic plots corresponding to a plurality of selected metabolites so as to screen the plurality of samples by associating at least one of the plurality of selected metabolites with the at least one plotted two-dimensional data set for each of the plurality of samples; and compare, for the screened plurality of samples determined to have the at least one of the plurality of selected metabolites associated therewith, the at least one plotted two-dimensional data set for each of the screened plurality of samples, across the screened plurality of samples, so as to determine a trend of the associated at least one of the plurality of selected metabolites, across the screened plurality of samples. A user interface 150 (see, e.g., FIG. 1) is in communication with the database and the processor device 130, wherein the user interface 150 is configured to display a visual indication of the comparison of the at least one plotted two-dimensional data set for each of the screened plurality of samples, across a plurality of the screened plurality of samples, to visually indicate the screened plurality of samples determined to have the at least one of the plurality of selected metabolites associated therewith, and the trend corresponding thereto, across the plurality of the screened plurality of samples. The processor device 130 is further configured to cooperate with the user interface 150 to sort the comparison of the at least one plotted two-dimensional data set for each of the screened plurality of samples, across a plurality of the screened plurality of samples, by the at least one of an experimental factor, a sample factor, and a process factor associated with the corresponding two-dimensional data set, so as to visually indicate the screened plurality of samples determined to have the at least one of the plurality of selected metabolites associated therewith, and the trend corresponding thereto, across the plurality of the screened plurality of samples, in relation to the at least one of an experimental factor, a sample factor, and a process factor.

Still further aspects of the present invention are directed to additional measures related to the disclosed further verification/confirmation principle for analyzing metabolomics data. For example, as shown in FIG. 7A, each of the screened plurality of samples determined to have the at least one of the plurality of selected metabolites associated therewith, may be associated with at least one information source related thereto, as implemented through cooperation, for example, between the processor device 130 and the database. Such information sources may comprise, for example, the database as it relates to the at least one of an experimental factor, a sample factor, and a process factor associated with the originally-collected data (i.e., an experimental factor information source, a sample factor information source, and/or a process factor information source), or the database as it relates to the originally-collected data itself (i.e., including, but not limited to, raw data corresponding to one of the screened plurality of samples determined to have the at least one of the plurality of selected metabolites associated therewith, wherein such raw data may include information, for example, on chromatographic peak shape, integration, primary spectra, and MS2 spectra (where applicable)—see, e.g., FIGS. 7B and 7C). From such an information source, it may be possible, for example, to examine various sources of influence on one or more of the screened plurality of samples determined to have the at least one of the plurality of selected metabolites associated therewith, so as to determine, for instance, machine/analytical device level outliers that may be responsible for the characteristics of the resulting post-analysis data. Even further, in some instances, this "lower level" information source may be used to determine, for example, the efficacy of a particular analytical device in providing reliable and consistent data with respect to the analyzed sample. In other instances, the at least one information source may comprise, for example, a chemical library (i.e., a chemical library information source) including chemical-specific information related to a particular selected (identified) metabolite, or in some instances, a compound formed of a combination of selected metabolites, wherein such chemical-specific information may include molecular weight, fragmentation data, etc. Still another contemplated information source may comprise publicly or otherwise accessible databases (e.g., a public chemical database) containing expanded information (i.e., publications, research results, etc.) related to a particular selected (identified) metabolite, or in some instances, a compound formed of a combination of selected metabolites, wherein such accessible databases may include, for instance, PubMed, Kegg, etc.

As further shown in FIG. 7A, the at least one information source may be accessed through, for example, a "drop down" menu 740 that may be associated, for instance, with the displayed visual indication of the comparison of the at least one plotted two-dimensional data set for each of the screened plurality of samples, across a plurality of the screened plurality of samples, that visually indicate the screened plurality of samples determined to have the at least one of the plurality of selected metabolites associated therewith, and the trend corresponding thereto, across the plurality of the screened plurality of samples 700. More particularly, since the comparison may ostensibly indicate at least one selected metabolite associated with the analyzed samples, a selected information source may indicate, for example, a corresponding chemical structure 710 of the at least one selected metabolite, chemical details 720 regarding the at least one selected metabolite, and/or a characteristic spectrum or characteristic plot 730 of the at least one selected metabolite. In other instances, the at least one information source may be accessed by selecting one of the screened plurality of samples from the displayed visual indication of the comparison of the at least one plotted two-dimensional data set for each of the screened plurality of samples, across a plurality of the screened plurality of samples, as implemented through cooperation, for example, between the processor device 130 and the database. The selected one of the screened plurality of samples may comprise, for instance, an "outlier" which may have a different one or more of the selected metabolites associated therewith than the one or more metabolites associated with the overall population of samples. In such instances, the two-dimensional data set corresponding to the selected one of the screened plurality of samples may be displayed in place of the overall comparison such that the selected one of the screened plurality of samples may be directly compared, on a visual or other basis to the at least one selected metabolite determined to be present therein (see, e.g., FIGS. 7B and 7C). As previously, any further examination of the post-analysis data may be facilitated by the at least one of an experimental factor, a sample factor, and a process factor originally associated with the as-collected data.

FIG. 8 illustrates yet another additional measure related to the disclosed further verification/confirmation principle for analyzing metabolomics data. More particularly, in some instances, it may be desirable to supplement the verification/confirmation of the post-analysis results by examining, for example, other metabolites or related chemicals that may be associated with one or more of the particular selected metabolites determined to be present in the plurality of samples in the sample population. As such, the "information source" aspect previously disclosed may be expanded to further encompass a relational component configured to relate metabolites and related chemicals and/or biochemicals according to a particular pathway, as implemented through cooperation, for example, between the processor device 130, the user interface 150, and the database. That is, for example, a "chemical library" may include chemical entries that are related according to various factors such as, for instance, an association with a particular metabolic process, and such a relationship may be accessible by the user in a tabular form (e.g., as shown in FIG. 8) or otherwise, during the further verification/confirmation process. In this regard, one skilled in the art will appreciate that the terms "metabolite," "biological," and "biochemical" as used in this context are generally encompassed under the "chemical" terminology otherwise referred to herein. As such, a method of analyzing metabolomics data, as otherwise disclosed herein may further include a procedure for screening the plurality of samples by associating a first metabolite of the plurality of selected metabolites with the at least one plotted two-dimensional data set for each of the plurality of samples, wherein the plurality of metabolites (and thus the first metabolite) are associated with a chemical pathway. In such an instance, the three-dimensional data set corresponding to each of a plurality of samples can then be analyzed for the presence (or absence) of a second metabolite, as implemented through cooperation, for example, between the processor device 130, the user interface 150, and the database, wherein the second metabolite is related to the first metabolite by the chemical pathway, so as to verify or otherwise confirm the association of the first metabolite with the at least one plotted two-dimensional data set for each of the plurality of samples.

In a similar aspect, once a selected metabolite has been determined to be present in a particular sample or sample population, it may sometimes be beneficial for the user to be able to examine other instances in which that selected metabolite has been identified, as a cross-reference or further consistency check with a particular analysis. As such, as shown schematically in FIG. 9, the "information source" aspect may be further expanded to encompass another relational component (i.e., database or archive) configured to relate a particular selected metabolite identified as being present in a particular sample or in the sample population, to completed studies (whether related or not, or similar or not) where the same selected metabolite may also have been identified as being present in the analyzed sample or sample population, as implemented through cooperation, for example, between the processor device 130, the user interface 150, and the database. That is, for example, at least one study factor of the three-dimensional data set corresponding to each of a plurality of samples and having the at least one of the plurality of selected metabolites associated therewith, as determined for a particular study, may be compared with a corresponding at least one study factor of another three-dimensional data set corresponding to each of a plurality of samples and having the at least one of the plurality of selected metabolites associated therewith, as determined for a previous study, so as to determine an inter-study relation therebetween. In this manner, various study factors such as, for example, the context of the study, the analyzed sample matrices, the effect or manifestation of the particular selected metabolite with respect to a certain disease state, etc. can be compared between studies as a cross reference or further consistency check with respect to the analyzed data.

In a further aspect, once a selected metabolite has been determined to be present in a particular sample or sample population, it may sometimes be beneficial for the user to be able to visually examine the effect of various sample-related factors on the post-analysis results. As such, as shown schematically in FIG. 10, the processor device 130 may be further configured to cooperate with the user interface 150, and the database so as to allow an axis parameter of the comparison (i.e., the sample-related factor plotted with respect to the x-axis) of the at least one plotted two-dimensional data set for each of the screened plurality of samples, across a plurality of the screened plurality of samples, to be varied so as to visually indicate to the user an effect of the particular sample-related factor associated with that axis parameter, across the plurality of the screened plurality of samples. For example, such variation of the x-axis parameter of the comparison may be implemented, for example, between the processor device 130, the user interface 150, and the database, by changing the x-axis parameter to or between such sample-related parameters as, for instance, a retention index, a retention time, a peak area, and a metabolite mass. Accordingly, such a capability further facilitates an evaluation of the confidence or certainty of the post-analysis results regarding identification of the one or more selected metabolites, and allows other sample-related factors to be additionally analyzed to supplement cross reference or further consistency information with respect to the analyzed data.

In addition to providing appropriate apparatuses and methods, embodiments of the present invention may also provide associated computer program products for performing the functions/operations disclosed above. Such computer program products may include a computer readable storage medium having appropriate computer readable program code embodied in and stored by the medium, and executable or otherwise accessible by an appropriate computer device.

With reference to FIG. 3, the computer readable storage medium may be, for example, part of the memory device 140, and may implement the computer readable program code to perform the above discussed operations.

In this regard, FIG. 3 is a block diagram illustration of methods, systems and computer program products according to embodiments of the invention. It will be understood that each block or step of the block diagram and combinations of blocks in the block diagram can be implemented by appropriate computer program instructions. These computer program instructions may be loaded onto a computer device or other programmable apparatus for executing the functions specified in the block diagram, flowchart or control flow block(s) or step(s), otherwise associated with the method(s) disclosed herein. These computer program instructions may also be stored in a computer-readable memory, so as to be accessible by a computer device or other programmable apparatus to function in a particular manner, such that the instructions stored in the computer-readable memory produce an article of manufacture capable of directing or otherwise executing instructions which implement the functions specified in the block diagram, flowchart or control flow block(s) or step(s), otherwise associated with the method(s) disclosed herein. The computer program instructions may also be loaded onto a computer device or other programmable apparatus to cause a series of operational steps to be performed on the computer device or other programmable apparatus to produce a computer-implemented process such that the instructions executed by the computer device or other programmable apparatus provide or otherwise direct appropriate steps for implementing the functions specified in the block diagram, flowchart or control flow block(s) or step(s), otherwise associated with the method(s) disclosed herein.

Accordingly, blocks or steps of the block diagram, flowchart or control flow illustrations support combinations for performing the specified functions, combinations of steps for performing the specified functions, and/or program instruction for performing the specified functions. It will also be understood that each block or step of the block diagram, flowchart or control flow illustrations, and combinations of blocks or steps in the block diagram, flowchart or control flow illustrations, can be implemented by special purpose hardware-based computer systems which perform the specified functions or steps, or combinations of special purpose hardware and computer instructions (software).

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of analyzing metabolomics data, comprising:
   automatically receiving, in a database, a three-dimensional data set of metabolomics data corresponding to each of a plurality of samples, from each of a first data source and a second data source;
   for the metabolomics data from each of the first and second data sources:
      converting the three-dimensional data set into at least one corresponding two-dimensional data set for each of the plurality of samples;

plotting the at least one two-dimensional data set for each of the plurality of samples;
comparing the at least one plotted two-dimensional data set for each of the plurality of samples to a plurality of characteristic plots corresponding to a plurality of selected metabolites so as to screen the plurality of samples by associating at least one of the plurality of selected metabolites with the at least one plotted two-dimensional data set for each of the plurality of samples; and
comparing, for the screened plurality of samples determined to have the at least one of the plurality of selected metabolites associated therewith, the at least one plotted two-dimensional data set for each of the screened plurality of samples, across the screened plurality of samples, so as to determine a trend of the associated at least one of the plurality of selected metabolites, across the screened plurality of samples;
displaying a visual indication of the comparison of the at least one plotted two-dimensional data set for each of the screened plurality of samples, across a plurality of the screened plurality of samples, to visually indicate the screened plurality of samples determined to have the at least one of the plurality of selected metabolites associated therewith, and the trend corresponding thereto, across the plurality of the screened plurality of samples, for the metabolomics data from each of the first and second data sources; and
comparing the first and second data sources with respect to the at least one of the plurality of selected metabolites determined to be included in the metabolomics data and the trend across the screened plurality of samples associated therewith so as to determine an identity confidence measure associated with the at least one of the plurality of selected metabolites.

2. A method according to claim 1, wherein the automatically receiving step further comprises:
compiling the three-dimensional data sets from the plurality of samples into a population data set; and
indexing the three-dimensional data sets by sample.

3. A method according to claim 1, wherein the visual indication comprises a plot of corresponding ones of the at least one plotted two-dimensional data set for each of the plurality of the screened plurality of samples versus a characteristic time at which a characteristic intensity peak of the at least one of the plurality of selected metabolites is expected.

4. A method according to claim 3, further comprising
retrieving the at least one plotted two-dimensional data set corresponding to each of a subset of samples lacking the characteristic intensity peak of the at least one of the plurality of selected metabolites at the characteristic time; and
displaying the at least one plotted two-dimensional data set corresponding to each of the subset of samples for subjective evaluation.

5. A method according to claim 3, wherein the step of comparing the at least one plotted two-dimensional data set for each of the screened plurality of samples, further comprises comparing a characteristic time at which a characteristic intensity peak associated with the at least one of the plurality of selected metabolites is expected in the at least one plotted two-dimensional data set for each of the screened plurality of samples, across the screened plurality of samples, so as to determine a trend of the associated at least one of the plurality of selected metabolites, across the screened plurality of samples.

6. A method according to claim 1, wherein the automatically receiving step further comprises automatically receiving a three-dimensional data set of metabolomics data corresponding to each of a plurality of samples from each of a first data source and a second data source, each of the first and second data sources comprising a chromatograph.

7. A method according to claim 1, wherein the automatically receiving step further comprises automatically receiving a three-dimensional data set of metabolomics data corresponding to each of a plurality of samples from each of a first data source and a second data source, each of the first and second data sources comprising one of a gas chromatograph, a positive channel of a liquid chromatograph, and a negative channel of a liquid chromatograph.

8. A system for analyzing metabolomics data, comprising:
a database in communication with each of a first data source and a second data source, the database being configured to automatically receive a three-dimensional data set of metabolomics data corresponding to each of a plurality of samples, from each of the first and second data sources;
a processor device in communication with said database, said processor device being configured, for the metabolomics data from each of the first and second data sources, to:
convert the three-dimensional data set into at least one corresponding two-dimensional data set for each of the plurality of samples;
plot the at least one two-dimensional data set for each of the plurality of samples;
compare the at least one plotted two-dimensional data set for each of the plurality of samples to a plurality of characteristic plots corresponding to a plurality of selected metabolites so as to screen the plurality of samples by associating at least one of the plurality of selected metabolites with the at least one plotted two-dimensional data set for each of the plurality of samples; and
compare, for the screened plurality of samples determined to have the at least one of the plurality of selected metabolites associated therewith, the at least one plotted two-dimensional data set for each of the screened plurality of samples, across the screened plurality of samples, so as to determine a trend of the associated at least one of the plurality of selected metabolites, across the screened plurality of samples; and
a user interface in communication with said database and said processor device, the user interface being configured to display a visual indication of the comparison of the at least one plotted two-dimensional data set for each of the screened plurality of samples, across a plurality of the screened plurality of samples, to visually indicate the screened plurality of samples determined to have the at least one of the plurality of selected metabolites associated therewith, and the trend corresponding thereto, across the plurality of the screened plurality of samples, for the metabolomics data from each of the first and second data sources, the displayed visual indication being further configured to facilitate determination of an identity confidence measure associated with the at least one of the plurality of selected metabolites from a comparison of the first and second data sources with respect to the at least one of the plurality of selected metabolites determined to be included in the metabolomics data and the trend across the screened plurality of samples associated therewith.

9. A system according to claim 8, further comprising a memory device in communication with said database and said processing device, the memory device being configured to store the plurality of characteristic plots.

10. A system according to claim 8, wherein each of the first and second data sources is selected from the group consisting of:
   a nuclear magnetic resonance imaging device;
   a spectrometry device;
   an electrochemical array device;
   a chromatograph; and
   combinations thereof.

11. A system according to claim 8, wherein each of the first and second data sources comprises one of a gas chromatograph, a positive channel of a liquid chromatograph, and a negative channel of a liquid chromatograph.

12. A system according to claim 8, wherein the database is further configured to compile the three-dimensional data sets from the plurality of samples into a population data set, and to index the three-dimensional data sets by sample, upon automatically receiving the three-dimensional data sets from each of the first and second data sources.

13. A system according to claim 8, wherein the visual indication displayed by the user interface further comprises a plot of corresponding ones of the at least one plotted two-dimensional data set for each of the plurality of the screened plurality of samples versus a characteristic time at which a characteristic intensity peak of the at least one of the plurality of selected metabolites is expected.

14. A system according to claim 13, wherein the processing device is further configured to retrieve the at least one plotted two-dimensional data set corresponding to each of a subset of samples lacking the characteristic intensity peak of the at least one of the plurality of selected metabolites at the characteristic time, and to displaying the at least one plotted two-dimensional data set corresponding to each of the subset of samples on the user interface for subjective evaluation.

15. A system according to claim 13, wherein the processing device is further configured to compare a characteristic time at which a characteristic intensity peak associated with the at least one of the plurality of selected metabolites is expected in the at least one plotted two-dimensional data set for each of the screened plurality of samples, across the screened plurality of samples, so as to determine a trend of the associated at least one of the plurality of selected metabolites, across the screened plurality of samples.

* * * * *